US 7,376,459 B2

(12) United States Patent
Rosenfeld

(10) Patent No.: US 7,376,459 B2
(45) Date of Patent: May 20, 2008

(54) SYSTEM AND METHOD FOR P300-BASED CONCEALED INFORMATION DETECTOR HAVING COMBINED PROBE AND TARGET TRIALS

(75) Inventor: J. Peter Rosenfeld, 1094 Linda La., Glencoe, IL (US) 60022

(73) Assignee: J. Peter Rosenfeld, Glencoe, IL (US)

( * ) Notice: Subject to any disclaimer, the term of this patent is extended or adjusted under 35 U.S.C. 154(b) by 234 days.

(21) Appl. No.: 11/224,523

(22) Filed: Sep. 12, 2005

(65) Prior Publication Data
US 2007/0049844 A1 Mar. 1, 2007

Related U.S. Application Data

(60) Provisional application No. 60/708,727, filed on Aug. 15, 2005.

(51) Int. Cl.
*A61B 5/04* (2006.01)
(52) U.S. Cl. .................. 600/544; 600/558; 600/559
(58) Field of Classification Search ............... 600/300, 600/301, 309, 544, 545, 558, 559
See application file for complete search history.

(56) References Cited

U.S. PATENT DOCUMENTS 2,944,542 A  7/1960  Barnett et al. ............... 128/688

(Continued)

OTHER PUBLICATIONS

Johnson, R. Jr. Simon, E.J., Henkell, H. and Fresiello, V.A."Cognitive and Neural Basis of Deceptive Responding About Attitudes and Beliefs: An event-related potential study". Paper presented at the Forty-Fourth Annual Meeting of the Society for Psychophysiological Research. Santa Fe. NM, 2004. *Psychophysiology*, 41, 2004, S63. 1 page.

(Continued)

*Primary Examiner*—Robert L. Nasser, Jr.
*Assistant Examiner*—Patricia Mallari
(74) *Attorney, Agent, or Firm*—James L. Katz; Brinks Hofer Gilson & Lione

(57) ABSTRACT

A system and method of deception detection is disclosed wherein T trials are combined with P and I trials. Denoted as the complex trial (CT) protocol, in one embodiment, the beginning of each trial is indicated by the onset of a stimulus which is either a P or I, which remains on the display terminal for particular random (unpredictable to the subject) time period. At the expiration of the period, the stimulus remains on the screen, but is altered/augmented in some way, such as by color change. The subject has been instructed that if the color change is to green, for example, the trial is a target trial, and the subject should make a "yes" (target) response. If the color is anything else (e.g., red, blue, yellow), the subject must give a "no" (non-target) response. Accordingly, in the CT protocol, the subject must attend even more intensely than in prior 3-stimulus protocols to the probe-irrelevant attribute (i.e., the color change) of the initially presented stimulus, because the target/non-target attribute is brief and its appearance is made unpredictable via the randomly varying property of the presentation time period. That is, the subject must keep fixating on the white stimulus, or else he will miss the target/non-target presentation. He is aware, as before, that missed targets and non-targets will betray lack of cooperation with the procedure. Further, the disclosed system and method promotes maintained vigilant attentiveness thereby reducing the effectiveness of countermeasures.

43 Claims, 17 Drawing Sheets

U.S. PATENT DOCUMENTS

| | | | |
|---|---|---|---|
| 3,163,486 A | 12/1964 | Tomes | |
| 3,548,806 A | 12/1970 | Fisher | |
| 3,574,450 A | 4/1971 | White et al. | 128/731 |
| 3,893,450 A | 7/1975 | Ertl | 128/731 |
| 3,901,215 A | 8/1975 | John | 128/731 |
| 3,971,034 A | 7/1976 | Bell, Jr. et al. | 128/630 |
| 4,188,956 A | 2/1980 | John | 128/731 |
| 4,216,781 A | 8/1980 | John | 128/731 |
| 4,331,160 A | 5/1982 | Zito, Sr. | |
| 4,493,327 A | 1/1985 | Bergelson et al. | 128/731 |
| 4,579,125 A | 4/1986 | Strobl et al. | 128/733 |
| 4,610,259 A | 9/1986 | Cohen et al. | 128/731 |
| 4,649,482 A | 3/1987 | Raviv et al. | 128/731 |
| 4,699,153 A | 10/1987 | Shevrin et al. | 128/745 |
| 4,736,751 A | 4/1988 | Gevins et al. | |
| 4,932,416 A | 6/1990 | Rosenfeld | 128/731 |
| 4,941,477 A | 7/1990 | Farwell | |
| 4,987,903 A | 1/1991 | Keppel et al. | |
| 5,113,870 A | 5/1992 | Rosenfeld | |
| 5,137,027 A | 8/1992 | Rosenfeld | |
| 5,170,780 A | 12/1992 | Rosenfeld | |
| 5,363,858 A | 11/1994 | Farwell | 128/731 |
| 5,406,956 A * | 4/1995 | Farwell | 600/544 |
| 5,450,855 A | 9/1995 | Rosenfeld | |
| 5,467,777 A | 11/1995 | Farwell | |
| 5,564,433 A | 10/1996 | Thornton | |
| 5,622,181 A | 4/1997 | Rosenfeld | |
| 5,752,922 A | 5/1998 | Rosenfeld | |
| 5,762,611 A | 6/1998 | Lewis et al. | |
| 5,797,853 A | 8/1998 | Musha et al. | |
| 5,846,207 A | 12/1998 | Rosenfeld | |
| 5,857,979 A | 1/1999 | Ryu et al. | |
| 5,876,334 A * | 3/1999 | Levy | 600/300 |
| 5,957,859 A | 9/1999 | Rosenfeld | |
| 2002/0188217 A1 | 12/2002 | Farwell | |
| 2003/0032870 A1 | 2/2003 | Farwell | |
| 2005/0143629 A1* | 6/2005 | Farwell | 600/300 |

OTHER PUBLICATIONS

Johnson, Jr., Barnhardt & Zhu, "Differential effects of practice on the executive processes used for truthful and deceptive responses: An event-related brain potential study", research report, Science d Direct, Cognitive Brain Research 24 (2005) pp. 386-404.

Johnson, Jr., Barnhardt & Zhu, "The contribution of executive processes to deceptive responding", article, Neuropsychologia 42 (2004) pp. 878-901.

Johnson, Jr., Barnhardt & Zhu, "The deceptive response: effects of response conflict and strategic monitoring on the late positive component and episodic memory-related brain activity", article, Biological Psychology 64 (2003) pp. 217-253.

J. P. Rosenfeld, "Alternative Views of Bashore and Rapp's (1993) Alternatives to Traditional Polygrapy: A Critique", Psychological Bulletin, 1995, vol. 117, No. 1 pp. 159-166.

Johnson and Rosenfeld, "Oddball-evoked P300-based method of deception detection in the laboratory II: Utilization of non-selective activation of relevant knowledge", International Journal of Psychophysiology, 12 (1992) pp. 289-306.

Rosenfeld, Angell, Johnson and Qian, "An ERP-Based, Control-Question Lie Detector Analog: Algorithms for Discriminating Effects Within Individuals' Average Waveforms", vol. 28, No. 3, Psychophysiology Copyright © 1991 by the Society for Psychophysiological Research, Inc., pp. 319-335.

Ellwanger, Rosenfeld, Sweet and Bhatt, "Detecting simulated amnesia for autobiographical and recently learned information using P300 event-related potential", publication reprinted from International Journal of Psychophysiology, 1996, pp. 9-23.

Rosenfeld, Soskins Bosh and Ryan, "Simple, effective countermeasures to P300-based tests of detection of concealed information", Psychophysiology, 41 (2004), pp. 205-219. Blackwell Publishing Inc. Printed in the USA. Copyright © 2004 Society for Psychophysiological Research.

Soskins, Rosenfeld and Niendam, "Peak-to-peak measurement of P300 recorded at 0.3 Hz high pass filter settings In Intraindividual diagnosis: complex vs. simple paradigms", International Journal of Psychophysiology 40 (2001) pp. 173-180. © 2001 Elsevier Science B.V.

Farwell and Donchin, "The Truth Will Out: Interrogative Polygraphy ("Lie Detection") With Event-Related Brain Potentials", Phychophysiology, Copyright © 1991 by The Society for Physchophysiolgical Research, Inv. vol. 28, No. 5, pp. 531-547.

Kramer, Sirevaag and Braune, "A Psychophysiological Assessment of Operator Workload During Simulated Flight Missions", © 1987, The Human Factors Society, Inc. pp. 145-160.

Rosenfeld, Lui, Skogsberg and Scher, "A Novel P300-based, concealed information detector (P3CIT): Combined Probe-or-Irrelevant and Target trials", Abstract for '05 SPR meetings in Lisbon, Oct. 2005, 18 pages.

Poster Session Abstract—*Psychophysiology* vol. 42 issue S1 p. S30-S134—Sep. 2005, doi: 10.1111/j.1469-8986.2005.00342.x.

Fischler, Bloom, Childers, Arroyo and Perry, "Brain Potentials During Sentence Verification: Late Negativity and Long-Term Memory Strength", article, Neuropsychologia, vol. 22, No. 5, pp. 559-568, 1984.

Fischler, Bloom, Childers, Roucos and Perry, "Brain Potentials Related to Stages of Sentence Verification", article, Psychophysiology, Copyright © 1983 by The Society for Psychophysiological Research, Inc., vol. 20, No. 4, pp. 400-409.

Donchin, "Presidential Address, 1980 Suprisel . . . Surprise?", , article, Psychophysiology, Copyright © 1981 by The Society for Psychophysiological Research, Inc., vol. 18, No. 5, pp. 493-513.

SPR Abstracts, 1985, vol. 22, No. 5, pp. 588-589.

Fabiani, Karis & Donchin, "P300 and Recall in an Incidental Memory Paradigm", Psychophysiology, Copyright © 1986 by The Society for Psychophysiological Research, Inc., vol. 23, No. 3, pp. 298-308.

Sutton, Braren, Zuben & John, "Evoke-Potential Correlates of Stimulus Uncertainty", Science, 150: pp. 1187-1188 (1965).

Karis. D. et al. (1984), "P300 and Memory", abstract, 1985, pp. 2-83.

Fabiani, Karis, & Donchin "Effects of Strategy Manipulation on P300 Amplitude in a von Restorff Paradigm", Twenty-Fifth meeting of the Society for Psychopysiological Research, Houston, TX, Oct. 17-20, 1985, 15 pages.

Neville, Snyder, Woods & Galambos, "Recognition and surprise alter the human visual evoked response", publication Proc. Natl. Acad. Sci. USA vol. 79, pp. 2121-2123, Mar. 1982.

Pritchard, Brandt and Barratt, "Analyzing Event-Related Potentials: The Utility of High and Low Pass Filtering in Improving the Relationship Between Various Amplitude Measures and Principal Components Analysis Factor Scores", article, Physchology Copyright © 1986 by the Society for Psychophysiological Research, Inc., vol. 23, No. 2, pp. 166-172.

Johnson, "P300: A Model of the Variables Controlling Its Amplitude", article, Annals New York Academy of Sciences, vol. 424, 1984, pp. 223-229.

Gomer, Spicuzza & O'Donnell, "Evoked potential correlates of visual item recognition during memory-scanning tasks", publication, Physiological Psychology, 1975, vol. 4 pp. 61-65.

Ford, Roth, Mohs, Hopkins and Kopell, "Event-Related Potentials Recorded from Young and Old Adults During a Memory Retrieval Task", publication, Electroencaphalography and Clinical Neurophysiology, 1979, 47: pp. 450-459.

Kramer, Schneider, Fisk and Donchin, "The Effects of Practice and Task Structure on Components of the Event-Related Brain Potential", publication, Psychophysiology, vol. 23, No. 1, Copyright © 1986 by The Society for Psychophysiological Research, Inc., pp. 33-47.

Adam and Collins, "Late Components of the Visual EvokedPotential to Search In Short-Term Memory", publication, , Electroencephalography and Clinical Neurophysiology, 1978, 44: pp. 147-156.

Geddes, Bourland, Smalling and Steinberg, "The Use of the Same Pair of Dry Electrodes to Record Skin Resistance and Beat-by-Beat Heart Rate", publication Medical and Biological Engineering, Jan. 1975, pp. 89-96.

Kleinmuntz, "Lie Detector Fail the Truth Test", article, Ideas for Action, Harvard Business Review, Jul.-Aug. 1985, pp. 36-37, 40-41.

Duncan-Johnson and Donchin, "On Quantifying surprise: The Variation of Event-Related Potentials With Subjective Probability", publication Psychophysiology, Copyright © 1977 by The Society for Psychophysiological Research, vol. 14, No. 5, pp. 456-467.

Neville, Kutas, Chesney and Schmidt, "Event-Related Brain Potentials During Initial Encoding and Recognition Memory of Congruous and Incongruous Words", publication, Journal of Memory and Language 25, 1986, 9 pages.

Kleinmuntz and Szucko, "Lie Detection and Ancient and Modern Times", publication American Psychologist, Jul. 1984, vol. 29, No. 7, pp. 766-776.

Saxe, Dougherty and Cross, "The Validity of Polygraph Testing", publicatin, American Psychologist, Mar. 1985, vol. 40, No. 3, pp. 355-366.

"Multidisciplinary Perspective in Event-Related Brain Potential Research", Proceedings of the Fourth International Contrass on Event-Related Slow Potentials of the Brain, Hendersonville, NC, Apr. 4-10, 1976, 12 pages.

Lykken, "The GSR in the Detection of Guilt", publication, Reprinted from *The Journal of Applied Psychology*, vol. 43, No. 6, 1959, 6 pages.

Fischler, Childers and Perry, "Effects of Scentence Form and Content on Late Potentials During Sentence Verification", article, pp. 109-110. 1986.

Kramer, Sirevaag and Braune, "A Psychophysiological Assessment of Operator Workload During Simulated Flight Missions", publication, Human Factors, 1987, 29(s), pp. 145-160.

Donchin, Kramer and Wickens, "Chapter Twenty-Six—Applications of Brain Event-Related Potentials to Problems in Engineering Psychology", 1982, pp. 702-718.

Ellwanger, Rosenfeld, Bermann, Nolan, Reinhart and Sweet, "Revised, Combined Oddball and Matching-to-Sample Procedure for Detection of Simulated Cognitive Deficit with P300: Deception-Specific Amplitude Distributions", article, Spring 1996, 18 pages.

Nies and Sweet, "Neuropsychological Assessment and Milingering: A Critical Review of Past and Present Strategies", publication, Archies of Clinical Neuropsychology, vol. 9, No. 6, pp. 501-552, 1994.

Hiscock and Hiscock, "Refining the Forced-Choice Method for Detection of Malingering", brief report, Journal of Clinical Experimental Neuropsychology 1989, vol. 11, No. 6, pp. 967-974.

Guilmette, Hart, Giullano and Leininger, "Detecting Simulated Memory Impairment: Comparison of the Rey Fifteen-Item Test and the Hiscock Forced-Choice Procedure", article, The Clinical Neuropsychologist 1994, vol. 8, No. 3 pp. 283-294.

Guilmette and Giuliano, "Taking the Stand: Issues and Strategies in Forensic Neuropsychology", article, The Clinical Neuropsychologist 1991, vol. 5, No. 3, pp. 197-219.

Ruchkin, Grafman, Krauss, Johnson, Canoune and Ritter, "Event-related brain potential evidence for a verbal working memory deficit in multiple sclerosis", article, *Brain* (1994), 117, 289-305.

Rosenfeld "Scaled P300 Scalp Profiles in Detection of Deception" Sep. 2002, Report No. (DoDP102-R-0005). Department of Defense Polygraph Institute, Fort Jackson, SC, 83 pages.

Rosenfeld "Brain Fingerprinting:" A Critical Analysis, In Press 2005 for *The Scientific Review of Mental Health Practive*, pp. 1-35.

Rosenfeld, Firoschak and Furedy, "P300-based detection of concealed autobiographical versus incidentally acquired information in target and non-target paradigms", JA909 In press, *Internatioanl Journal of Psychophysiology*, 2005, pp. 1-31.

* cited by examiner

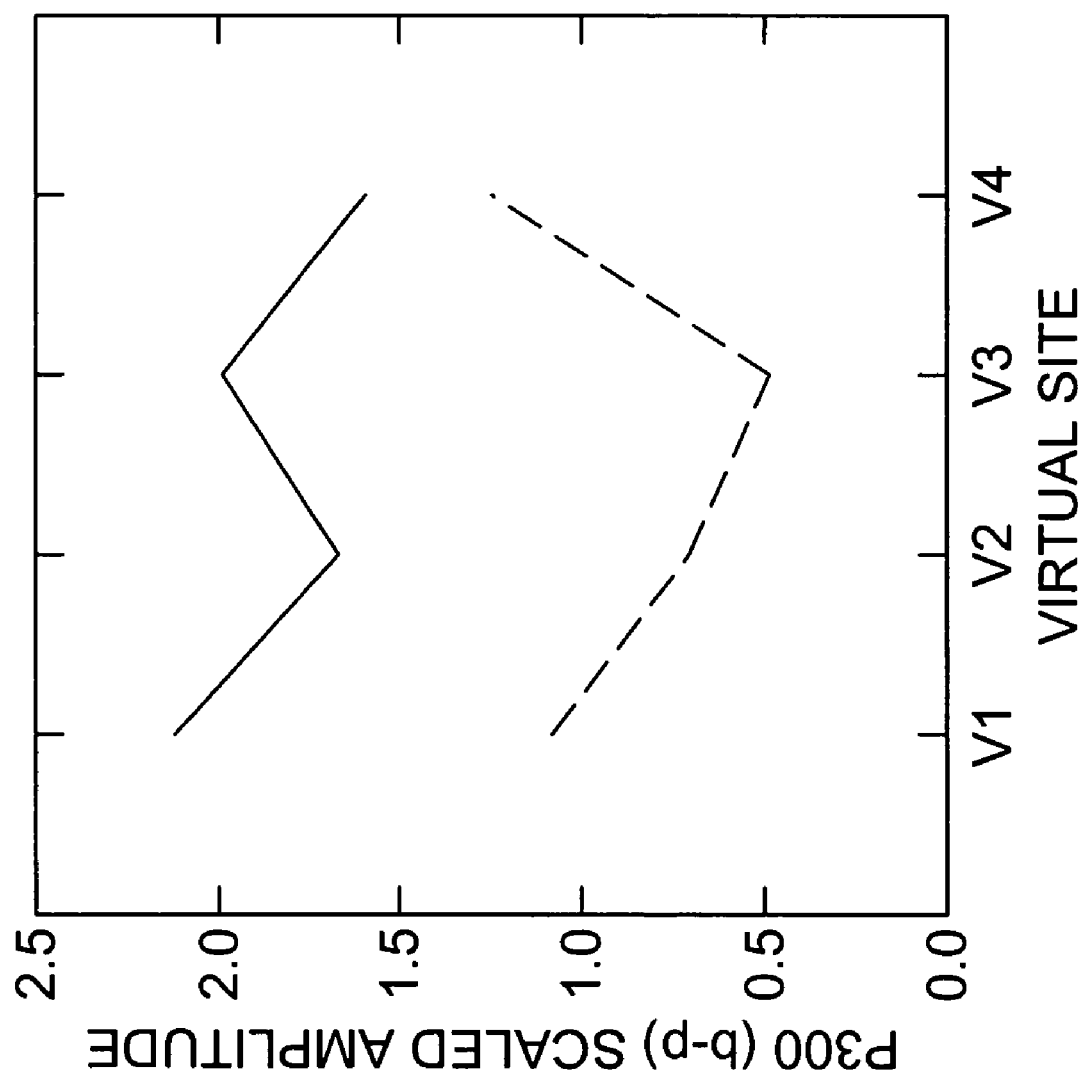

SYSTEM AND METHOD FOR P300-BASED CONCEALED INFORMATION DETECTOR HAVING COMBINED PROBE AND TARGET TRIALS

REFERENCE TO RELATED APPLICATIONS

This application claims the benefit of the filing date under 35 U.S.C. § 119(e) of U.S. Provisional Application Ser. No. 60/708,727 filed Aug. 15, 2005, which is hereby incorporated by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

An electroencephalograph (EEG) is a known device which senses, measures and records brain waves of a subject person by sensing spontaneous electrical potentials, typically referred to as EEG, and also by sensing event related potential ("ERP"), discussed in more detail below, existing at selected scalp sites and generated in the subject's cortex or cerebrum. Usually, an EEG is provided with a plurality of channels, and each EEG channel corresponds to a particular electrode combination attached to the subject. The ERPs sensed at each channel are amplified by a differential amplifier, and the amplifier output signal is recorded.

Historically, the output signal was originally used to control movement of a recording pen on advancing graph paper, as in a polygraph. The polygraph paper is driven at a predetermined rate (e.g., 30 millimeters per second) and is graduated to represent predetermined time increments. The EEG record produced is thus in the form of a long strip of polygraph paper containing a wave form for each EEG channel.

Contemporarily, an EEG can be functionally associated with a computer and the computer's memory device, such as a floppy disc or the like can be used to record the sensed ERPs.

A skilled neurologist can evaluate an EEG record to interpret abnormalities in the wave forms recorded. However, a suitably programmed computer that is functionally associated with an EEG can be used to evaluate EEG sensed signals.

Electrical signals produced by an EEG exhibit different frequencies depending upon the varying electrical activity of the human brain. The EEG signal frequencies detected are conventionally classified into four basic frequency bands, which are generally referred to as "Delta" (0.3-5 Hertz); "Theta" (4 to less than 8 Hertz); "Alpha" (8-13 Hertz); and "Beta" (greater than 13 Hertz). A neurologist or a programmed computer can determine the predominant frequency observed from a particular EEG channel during a particular time period by measuring the time period of the frequency of a given EEG signal wave form, or using various time series spectral analytic techniques such as Fourier series.

Since an EEG signal wave form typically includes multiple frequency components, ERP frequency determinations can be complicated procedures. However, electronically produced wave forms and computerized scanning techniques are recognized to substantially improve the objectivity and reliability of brain wave analysis, as those skilled in the art will appreciate. EEG measurable brain waves can be driven by specific extrinsic or endogenous events. For example, a single regularly occurring stimulus will elicit a series of electrical signals or brain waves each time it is presented. The entire series is referred to as an event-related potential ("ERP").

Both the frequency of a sensed ERP as well as the amplitude of its components are often analyzed. Significance has been established when brain waves of large amplitudes occur at time intervals of about 300 msec (milliseconds) or more after the eliciting event. One class of brain wave produced under such circumstances is known as P300 brain wave or, sometimes, more simply, as the P3 brain wave. The P3 brain wave is a positive deflection in the EEG of a subject electroencephalographically preferably recorded either from the CZ or the PZ cranial positions and with an amplitude typically in the range of about 2 to about 20 microvolts measured from baseline to peak. A P3 wave is recorded in response to stimuli which are especially meaningful to a subject in any way and, in general, the more unexpected and rare the stimulus, the larger the amplitude of the P3 voltage.

Usually P3 is recordable from the CZ, FZ and PZ positions and is characteristically largest at PZ and smallest at FZ. See Donchin, E., Ritter, W. and M. Calloway, W. C. (1978), "Event Related Brain Potentials in Man", Calloway et al. ed., Academic Press, 1978. Production of such waves appears to be involuntary.

There is evidence to suggest that the P300 brain wave generating process inherently occurs when the updating, or "refreshing", of representations in working memory is required; see, for examples, Donchin, Psychophysiology. 18, 493-513 (1981); Fabiani, Karis and Donchin, Psychophysiology, 22, 588-589 (1985); and others. P300 brain waves of large amplitudes are now recognized to be characteristically elicited by rare or unexpected events, particularly when they are relevant to a task, such as information recognition, that a subject is performing.

It is theorized that reception of such an event by a subject may lead to restructuring or updating of the subject's working memory, and this activity is further theorized to be part of the ongoing process of maintaining accurate schemes of the environment; however, there is no wish to be bound by theory herein. The updating process, according to the theory, may lead to an "activation" of the representation, or to the "marking" of some attribute of the event that was crucial in determining the updating process.

This restructuring of the representation of an event is theorized to facilitate the subsequent recall of the event, by providing valuable retrieval cues. It now appears that the greater the restructuring that follows an individual event, the higher the probability of later recalling that event. If the P300 brain wave amplitude actually represents the degree of restructuring in a working brain memory, then the P300 brain wave amplitude should also characteristically predict capability for later recall; Fabiani, Karis and Donchin, Psychophysiology, 23, 298-308 (1986).

The existing knowledge about the frequency and the amplitude of brain waves and the advent of widespread usage of the programmed computer in behavioral neuroscience has made the analysis of EEG-generated data easier and capable of treatment by new methodology.

Oftentimes, it is desirable to have an objective method of determining whether or not a person has recallable knowledge of a particular fact, whether in a visual or other form, such as autobiographical information, a perpetrated act, or factual information concerning a weapon, a crime scene configuration, a secret document, a stolen object, data, another person's face, etc. Such knowledge as taught by certain prior art procedures and devices can be used in "guilty knowledge" and/or "comparison question" or "control question" assessment tests, subcategories of procedures used in physiological detection of deception ("lie detection"). Other kinds of detectable concealed information would be autobiographical knowledge that a head injury malingerer of cognitive deficit would want to pretend not to recall.

If, for example, a discreet, sensorially perceivable stimulus, such as a sound, a light flash, a body tap, or the like is presented to a human subject, his concurrently recorded electroencephalogram shows a series of time-locked brain wave responses called event related potentials ("ERP"). It was shown in the 1960's that if a subject is presented with a series or set comprised of stimuli of two types, e.g., a high tone and a low tone, and if either of those tones is presented in, for example, 20 of 100 trials (with the remaining 80 trials containing the other tone), the rare stimulus will cause production of a large ERP identified as a P3 or P300 brain wave, as such is above defined. In this so-called "odd-ball" paradigm, it was known that the P3 brain wave amplitude varies proportionally with rarity. See Sutton et al., Science, 150 1187-1188 (1965).

In the 1970's and thereafter, other workers reported that a P3 brain wave is produced by a subject when the subject has previously seen such a word (or picture) even when such word (or picture) is also accompanied or by novel or unrelated words (or pictures) relative to the original word or picture. Such unrelated words (or pictures) fail to produce a concurrent P3 brain wave in the subject. See Karis et al., Cognitive Psychology, 16. 177-216; Neville et al., Proc. Nat. Ac. Sci. U.S.A. 79, 2121-2123, (1982).

Sutton (supra) used subject P3 brain wave responses in an odd-ball paradigm procedure which employed simple auditory stimuli, e.g. high tones and low tones, that were presented singly and serially to subjects. Whatever tone was presented least often evoked production of a P3 brain wave response in a subject. Also, Pritchard et al., Psychophysiology, 23, 166-172 (1986) utilized an odd-ball paradigm in which each of the stimuli used was a simple visual flash which differed from others in the set in brightness. R. Johnson, Jr., Ann. of the N.Y. Acad. of Sci., 425, 223-230 (1984), like Pritchard, describe studies utilizing P3 brain wave production in response to memory updating processes, expectancy processes, surprise, perception, and the like.

Fabiani et al., Psychophysiology, 23, 298-308 (1986), and Neville et al. (supra) utilize verbal, meaningful stimuli in a variant kind of odd-ball paradigm bearing on recognition memory; however, these studies were not and could not be configured as field relevant, repetitively presented deception detection odd-ball paradigms because both novel and previously seen words (or pictures) in these studies were never repeated within the EEG run.

The average ERP voltage produced in response to previously seen words (or pictures) was an average of responses to a series of all different words (or pictures). Also, the average ERP voltage produced in response to novel words (or pictures) was an average of responses to all the different novel words (or pictures) comprising the paradigm set used. This kind of paradigm is currently believed to be specifically unsuited for use in real criminal-type investigations since, in such investigations, it is usually only a few items, such as the murder weapon, the stolen item, the classified document, or the like, which is the crucial evidence involved in a real crime.

The Fabiani et al. and the Neville et al. studies were directed at, and tailored to achieve, scientific elucidation of memory processes. In these studies, the repetition of words was avoided for fear of engaging habituation processes which would tend to reduce P3 brain wave amplitude effects. None of the prior art articles disclose use of an odd-ball paradigm which is serially and repetitively repeated, which is comprised of meaningful word stimuli, and which functions to detect concealed "guilty" knowledge or other recognition processes.

There are other studies reported in the literature which do not use quasi verbal stimuli which are repeatedly presented. A review of the literature reveals that these studies do not use odd-ball paradigms. In fact, such studies concern memory processes and use extremely complicated procedures which are tailored to these research purposes. See, for example, the studies reported by Gomer et al., Physio. Psych., 4, 61-65 (1976), (1976); Ford et al., Elect. Clin. Neuroph., 47, 450-459 (1979); Kramer et al., Psychophysiology, 23, 33-47 (1986); and Adam and Collins, Elec. Clin. Neuroph., 44, 147-156 (1978). All such studies actually use "go-no go", or pattern matching, paradigms. In such a paradigm, a set of letters or numbers is memorized by the subject who is then given a trial series in which he decides whether ("go") or not ("no go") a memorized target stimulus is presented. Other differences between these procedures and repetitively presented odd-ball paradigms exist.

Typically, the prior art reports subject P3 brain wave responses to both target and non-target stimuli. Although target P300 brain wave effects are often reported to be bigger, unambiguous use of subject P300 brain wave responses in field investigations of deception requires results which are virtually of the dichotomous kind, e.g. yes or no, guilty or not-guilty. Such results are not achievable in the prior art using such paradigms.

Further, the prior art studies use simple stimuli, such as digits or letters, rather than meaningful words, such as are needed for most real-life evaluations. However, the intent of the prior art methods was the elucidation of memory retrieval processes, not the detection of deception. Also, for such memory elucidation research purposes, P3 brain wave latency measurement may have been more important than P3 brain wave amplitude measurement.

Instruments have heretofore been used to determine psychological stress, such as, for example, the apparatus described in U.S. Pat. No. 2,944,542 which relates to a blood pressure measuring device that indicates variations in the velocity of pulse waves, thereby indicating a change in emotional estate. U.S. Pat. No. 3,971,034 describes a method and apparatus for identifying psychological stress by converting oral impulses into electrical signals and recording, observing and analyzing those signals. U.S. Pat. No. 3,893,450 relates to a method and apparatus for examining brain wave form by providing stimuli such as light and determining the characteristic of a mathematically determined point in the brain wave forms of the subject. U.S. Pat. No. 4,188,956 relates to a method of acquiring, compressing and analyzing neurometric test data by means of a digital computer base system. U.S. Pat. No. 4,579,125 relates to a method for processing analog EEG signals to provide an indication of cerebral activity.

Accordingly, system and method are needed which are suitable for determining subject P3 brain waves responses indicative of concealed information from a repeatedly presented stimulus or stimuli interspersed with non-significant stimuli, thereby to obtain reliable results directed towards evaluating control question, screening, guilty knowledge testing, attention level, pain and other phenomena involving a subject.

BRIEF DESCRIPTION OF THE DRAWINGS

FIG. 17 depicts scaled b-p, group-averaged values of 3 stimulus types at 4 virtual sites containing an obvious interaction.

DETAILED DESCRIPTION OF THE DRAWINGS AND PRESENTLY PREFERRED EMBODIMENTS

The disclosed embodiments relate to systems and methods which employ event-related potentials ("ERP") generated by a subject for purposes of detection and/or evaluation of the subject's undisclosed prior cognition and/or action. The disclosed systems and methods involve measuring and evaluating, such as by a computer, subject responses to a repeatedly serially presented information set of stimuli comprised of both significant and non-significant information. Further, the disclosed embodiments relate to systems and methods which are substantially resistant to, or allow for the substantial detection of, techniques designed to allow a subject to thwart the detection of deception, i.e. countermeasures.

To clarify the use in the pending claims and to hereby provide notice to the public, the phrases "at least one of <A>, <B>, . . . and <N>" or "at least one of <A>, <B>, . . . <N>, or combinations thereof" are defined by the Applicant in the broadest sense, superseding any other implied definitions herebefore or hereinafter unless expressly asserted by the Applicant to the contrary, to mean one or more elements selected from the group comprising A, B, . . . and N, that is to say, any combination of one or more of the elements A, B, . . . or N including any one element alone or in combination with one or more of the other elements which may also include, in combination, additional elements not listed.

It is well known that between an electrode placed on the scalp surface directly over brain and another electrode connected to a relatively neutral (electrically) part of the head (i.e., remote from brain cells, such as the earlobe), an electrical voltage, varying as a function of time, exists. These voltages comprise the spontaneously ongoing electroencephalogram or EEG, and are commonly known as brain waves. If during the recording of EEG, a discrete stimulus event occurs, such as a light flash or tone pip, the EEG breaks into a series of larger peaks and troughs lasting up to two seconds after the stimulus. These waves, signaling the arrival in cortex of neural activity generated by the stimulus, comprise the wave series called the ERP, the EEG potential series related to the stimulus event.

Actually, the ERP "rides on" the ongoing EEG, by which it is sometimes obscured in single trials. Thus, one typically averages the EEG samples of many repeated presentation trials of either the same stimulus or stimulus category (e.g., audibly or visually presented male names), and the ensuing averaged stimulus-related activity is revealed as the ERP, while the non-stimulus-related features of the EEG average out, approaching a straight, flat line. P300 is a special ERP which results whenever a meaningful piece of information is rarely presented as a stimulus among a random series of more frequently presented, non-meaningful stimuli.

Figure 1:
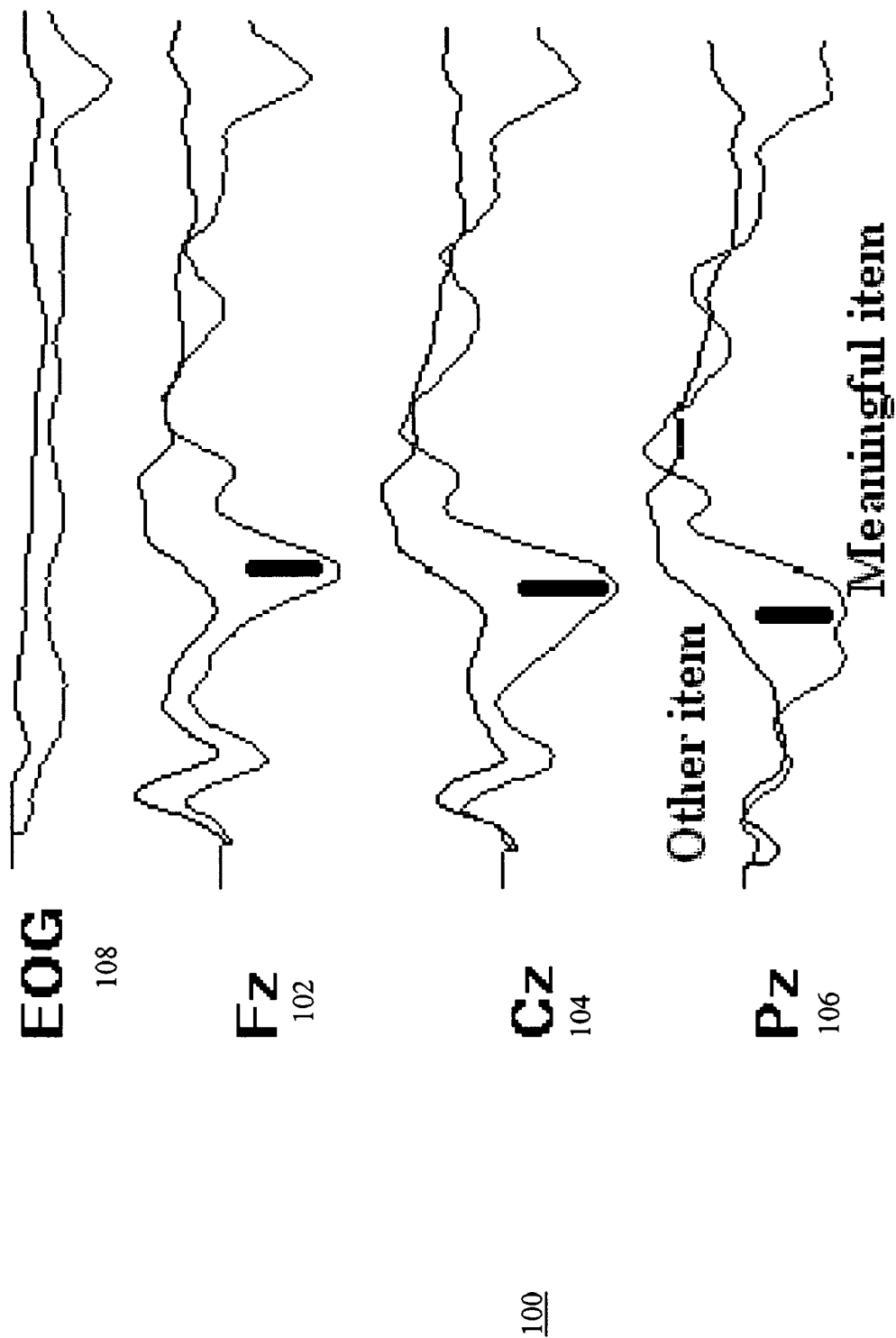
FIG. 1 depicts an exemplary set of three pairs of superimposed ERP averages.

For example, FIG. 1 shows a set 100 of three pairs of superimposed ERP averages from three scalp sites (called Fz 102, Cz 104, and Pz 106) on a single subject who was viewing a series of test items on a display screen (from Rosenfeld, J. P. Soskins, M., Bosh, G., & Ryan, A. (2004) Simple effective countermeasures to P300-based tests of detection of concealed information. Psychophysiology, 41, 205-219, hereafter "Rosenfeld et al., 2004"). On 17% of the trials, a meaningful item (e.g., the subject's birth date) was presented, and on the remaining 83% of the randomly occurring trials, other items with no meaning to the subject (e.g., other dates) were presented. The two superimposed waveforms at each scalp site represent averages of ERPs to 1) meaningful items and to 2) other (non-meaningful) items. In response to the meaningful items, a large down-going P300 110 (indicated with thick vertical lines) is seen which is absent in the superimposed other waveforms. (The wave labeled "EOG" 108 is a simultaneous recording of eye movement artifact activity. As required for sound EEG recording technique, these waves are flat during the segment of time when P300 occurs, indicating that no artifacts due to eye movements are occurring, which, if present, could account for apparent P300s.) Clearly, the rare, recognized meaningful items elicit P300, the other items do not. (Note that electrically positive brain activity is plotted down, as it is traditionally.) It should be evident that the ability of P300 to signal the involuntary recognition of meaningful information suggests that the wave could be used to signal concealed information such as "guilty knowledge" ideally known only to a guilty perpetrator and to police, or knowledge of prior acts known only by the guilty subject.

In all the brain-wave based deception detection methods discussed below, EEG was conventionally recorded as described below, though it will be appreciated that the disclosed system and method of inferring deception is not dependent upon the method in which a subject's brain waves are recorded or otherwise acquired and that other methods of recording and/or acquiring EEG or other suitable indicators of brain activity, both conventional and non-conventional may be used. For example, a magnetoencephalogram (MeG) may be utilized which records P300 expressed as a function of the magnetic fields associated with EEG voltages, and thereby provides a measure of P300 where no contact with the subject's skin is involved. Other brain activity indices, e.g., fMRI, PET, etc, are also possible to use with the disclosed CT paradigm to be described below.

Data Acquisition: In illustrative experiments described below, EEG was recorded with silver electrodes attached to sites Fz, Cz, and Pz. The scalp electrodes were referenced to linked mastoids. EOG was recorded with silver electrodes above and below the right eye, but laterally offset from one another by 1 cm. They were placed intentionally diagonally so they would pick up both vertical and horizontal eye movements, as verified in pilot study and used in several subsequent studies (e.g., Rosenfeld et al., 2004). The artifact rejection criterion was 80 µV. The EEG electrodes were referentially recorded but the EOG electrodes were differentially amplified. The forehead was grounded. Signals were passed through Grass P511K amplifiers with a 30 Hz low pass filter setting, and a high pass filters set (3 db) at 0.3 Hz. Amplifier output was passed to a 12-bit Keithly Metrabyte A/D converter sampling at 125 Hz. For all analyses and displays, single sweeps and averages were digitally filtered off-line to remove higher frequencies; 3 db point=4.23 Hz. P300 was measured in two ways, the first of which is the Base-peak method ("b-p"): This standard algorithm searches within a window from 400 to 900 ms for the maximally positive segment average of 104 ms. The pre-stimulus 104 ms average is also obtained and subtracted from the maximum positivity to define the b-p measure. (104 ms is the product of the 13 data points devoted to pre-stimulus baseline and the 8 ms resolution with our 125 Hz sampling rate.) The midpoint of the maximum positivity segment defines P300 latency. The second method for measuring P300 is the Peak-Peak ("p-p") method: After the algorithm finds the maximum positivity, it searches from P300 latency to 2000 ms for the maximum 104 ms negativity. The difference between the maximum positivity and negativity defines the p-p measure. We have repeatedly shown that using a bootstrapped amplitude difference method (detailed below), p-p is a better index than b-p for diagnosis of guilt vs. innocence in p300 amplitude based deception detection (e.g., Soskins, M., Rosenfeld, J. P., & Niendam, T. (2001). The case for peak-to-peak measurement of P300 recorded at 0.3 hz high pass filter settings in detection of deception. Int. J. Psychophysiology, 40, 173-180, hereafter "Soskins et al., 2001").

The brain wave based deception detection tests in the prior art all have at least two not necessarily independent attributes: 1) The protocol for data collection and 2) The method of data analysis. Both of these attributes can differ in multiple sub-attributes. Slight differences in sub-attributes can be qualitative or quantitative. The best way to understand these abstract points is with the aid of basic examples.

The protocol used by the previous teachings for P300-based detection of concealed information (e.g., Rosenfeld, (U.S. Pat. Nos. 4,932,416; 5,113,870; 5,170,780; 5,622,181; 5,752,922; 5,846,207; and 5,957,859); Farwell, (U.S. Pat. Nos. 4,941,477; 5,363,858; 5,406,956; and 5,467,777), or Allen, Iacono & Danielson, 1992) are variants of the oddball paradigm known and utilized often in research to elicit the P300 event-related potential ("ERP"). See Fabiani, M., Gratton, G., Karis, D., & Donchin, E (1987), The definition, identification, and reliability of measurement of the P3 component of the event-related potential. In P. K. Ackles, J. R. Jennings, & M. G. H. Coles (Eds.), Advances in psychophysiology Vol. 2, Greenwich: JAI Press, hereafter "Fabiani & Donchin, 1987." In this 2-stimulus protocol, the subject may view the presentation of stimuli, one at a time, about 1 every 3 seconds, on a display screen. These stimuli may be a set of say 10 words, one of which has a special meaning for the subject, such as his name in a series of 10 other, less or non- meaningful names. The words are randomly and repeatedly presented in a Bernoulli series of approximately 100 or more stimuli, each having a probability of 0.1. The subject is given a response button panel and told to press a "yes" button only when he sees his name, and a "no" button in response to other names. There are other response style options: He may also press only for his name and make no responses to other names. Or he can silently count occurrences of only his name. If the EEG responses to his name presentations are averaged in any of these variant paradigms, a P300 will be seen in average response to the special (autobiographical name) stimulus because it is rare, and especially meaningful in 2 ways: it 1) is autobiographical and 2) requires a unique response. One can remove the response requirement and still see a P300 due only to the special autobiographical meaningfulness and rareness. A response requirement is typically used in some research to enhance the P300 size. It is the case that one can vary the total number of stimuli in the set to be <10, e.g., 3-9, and thereby change the oddball probability to be >0.1. Or one can use stimulus set sizes >10. One needs to average a minimum of 20 sweeps to obtain a clean, noise-free ERP average, but one could average any number >20 which would be feasible to present. These parametric changes in stimulus set size or trials per average exemplify "slight differences," as noted above. Likewise, variations in the use of the response requirement represent slight differences. It is noted that the other frequent, relatively meaningless stimuli—e.g., names other than those of the subject—in the stimulus set do not elicit a P300 seen in their average.

U.S. Pat. No. 4,932,416 to Rosenfeld (the "'416 patent") discloses a significant variation of this basic protocol, specially adapted for detection of deception. The total stimulus set size was 9. The specially meaningful stimulus was the name of an item secretly "stolen" from a box containing 9 items during a laboratory analog of a crime. It was, in other words, a mock crime detail. We will refer to this special guilty knowledge item as a probe (P). The other eight items were other non-stolen items also in the box, or in another embodiment, novel items, not seen previously in the box. We will refer to these as irrelevants (I), denoting irrelevants to the mock or pretend crime.

The '416 patent disclosed that there would need to be some way to force the attention of a real suspect,—eager to escape detection—of a real crime in a field situation, to the display screen, so that the Ps would be noticed and the P300 would be elicited by them, thereby revealing recognition of stolen items, knowledge of which would not be had by innocent subjects. Thus one of the 8 non-meaningful stimuli was designated as the target (T) stimulus, and subjects were instructed to give a "yes" response to the T stimulus, and "no" responses to all other stimuli, P and I's. Subjects were alerted that the failure to reliably give a yes response to T presentations would indicate a lack of cooperation with the test, heightening the suspicions of authorities in real world field situations. Since all three stimuli, P, I's, and T, were randomly repeated, one at a time on separate trials, and since subjects had to attend to each stimulus presentation so as not to miss T trials, the subject was thus compelled to attend to the stimulus on every trial, and would not, therefore, miss P occurrences. In this situation, both P and T elicited P300, which was not elicited by I's, in guilty subjects who had the knowledge of the crime-relevant (P) item. In innocent (control) subjects who lacked knowledge of stolen items, only Ts and neither P's nor I's elicited P300s. For an innocent subject, a P is just another I. Thus, the statistical tests used within each subject to determine guilt or innocence basically examine whether or not the P stimulus elicits P300; a simple way to do that is to statistically compare P300 to P and I stimuli. Various methods, taught in prior art, to do that are described in Rosenfeld et al., (2004). Here follows a summary of one such method:

Within individual diagnostic analysis: Bootstrapped amplitude difference method (SIZE): As this is a diagnostic deception detection method, we also diagnosed guilt or innocence within individuals. To determine whether or not the P300 evoked by one stimulus is greater than that evoked by another within an individual, the bootstrap method (Wasserman, S., & Bockenholt, U. (1989). Bootstrapping: Applications to psychophysiology. Psychophysiology, 26, 208-221, hereafter "Wasserman & Bockenholt, 1989") is usually used on the Pz site where P300 is typically largest. This will be illustrated with an example of a probe response being compared with an irrelevant response. The question answered by the bootstrap method is: "Is the probability more than 90 in 100 that the true difference between the average probe P300 and the average irrelevant P300 is greater than zero?" For each subject, however, one has available only one average probe P300 and one average irrelevant P300. Answering the statistical question requires distributions of average P300 waves, and these actual distributions are not available, since the experiment is run only once yielding one set of probe and irrelevants averages per subject. One thus bootstraps the distributions, in the bootstrap variation used here, as follows: A computer program goes through the probe set (all single sweeps) and draws at random, with replacement, a set of n1 waveforms. It averages these and calculates P300 amplitude from this single average using the maximum segment selection method as described above for both p-p and b-p indices. Then a set of n2 waveforms is drawn randomly with replacement from the irrelevant set, from which an average P300 amplitude is calculated. The number n1 is the actual number of accepted probe sweeps for that subject, and n2 is the actual number of accepted irrelevant sweeps for that subject. It is also possible to set n2=n1, and then randomly draw n1 samples from the irrelevant distribution. The calculated irrelevant mean P300 is subtracted from the comparable probe value, and one thus obtains a difference value to place in a distribution which will contain 100 values after 100 iterations of the process just described. Multiple iterations will yield differing (variable) means and mean differences due to the sampling-with-replacement process.

In order to state with 90% confidence (a typical criterion; Rosenfeld et al., 2004; Farwell, L. A., & Donchin, E. (1991), The truth will out: Interrogative polygraphy ("lie detection") with event-related potentials, Psychophysiology, 28, 531-547, hereafter "Farwell & Donchin, 1991") that probe and irrelevant evoked ERPs are indeed different, one requires that the value of zero difference or less (a negative difference) not be >−1.29 SDs below the mean of the distribution of differences. In other words, the lower boundary of the 90% confidence interval for the difference would be greater than 0. It is noted that sampling different numbers of probes and irrelevants (n1 doesn't =n2) could result in differing errors of measurement, however, studies have shown a false positive rate of zero utilizing this method (Ellwanger, J., Rosenfeld, J. P., Sweet, J. J. & Bhatt, M. (1996), Detecting simulated amnesia for autobiographical and recently learned information using the P300 event-related potential, International Journal of Psychophysiology, 23, 9-23, hereafter "Ellwanger et al., 1996") and others have taken a similar approach (Farwell & Donchin, 1991) with success. This method has the advantage of utilizing all the data, as would an independent groups t-test with unequal numbers of subjects. A one-tailed 1.29 criterion yields a $p<0.1$ confidence level because the hypothesis that the probe evoked P300 is greater than the irrelevant evoked P300 (which shows that the subject has guilty knowledge) is rejected either if the two are not found significantly different or if the irrelevant P300 is found larger. (T-tests on single sweeps are too insensitive to use to compare mean probe and irrelevant P300s within individuals; see Rosenfeld, J. P., Angell, A., Johnson, M., & Qian, J. (1991), An ERP-based, control-question lie detector analog: Algorithms for discriminating effects within individuals' average waveforms, Psychophysiology, 38, 319-335, hereafter "Rosenfeld et al., 1991.")

It is noted that the 3-stimulus (P,T,I) protocol represented a significant departure from the simple 2-stimulus protocol discussed above as the fundamental exemplar of the oddball paradigm. The 3-stimulus protocol used the novel T stimulus to force attention, and correctly assumed the previously novel fact that even though P's were being responded to just as I's were in guilty subjects, their special intrinsic meaning for guilty but not innocent subjects would still elicit P300s in the former, thus revealing their guilty knowledge.

If only one P stimulus in one block of trials were tested and revealed to elicit a P300, it would still be difficult to make the case that the subject was guilty because by chance, one stimulus might elicit a guilty response. Indeed the chance probability of one hit among 9 items is $1/9=0.1111$. There is thus a greater than 10% chance of a false positive diagnosis with just one block of trials containing just one probe. As argued by Lykken (Lykken, D. T. (1981), A tremor in the blood, New York: McGraw-Hill; Lykken, D. T. (1998), A tremor in the blood, Reading, Mass.: Perseus Books), for this reason, one likes to test a subject on multiple orthogonal crime details in these guilty knowledge protocols which he invented in 1959 (Lykken, D. (1959) The GSR in the detection of guilt, Journal of Applied Psychology, 43, 385-388.) using autonomic responses (vs. the present P300 responses), because the probability of a guilty response by chance on multiple stimuli becomes increasingly smaller as positive outcomes occur on multiple orthogonal items.

More quantitatively, supposing there is a crime involving 6 details, any one of which an investigator could test a guilty person for knowledge. Let us say one of those details is the amount of money stolen, and let us assume that it is fact $2000. One might then form a set of 5 dollar amounts: $1000, $2000 . . . $5000. The probability of a chance hit on any one of these 5 amounts is $1/5=0.2$. Thus if one tested subjects on these 5 amounts, each presented one at a time and established that a statistically reliable P300 was elicited by the $2000 amount, one might conclude that the subject tested had guilty knowledge. However, the probability that an innocent subject might by chance show a reliable P300 to the $2000 stimulus is finite and large at 0.2, meaning that 2 in 10 innocent subjects would be wrongly diagnosed. Moreover, perhaps one is dealing with a guilty subject who hasn't had a chance to count the money he stole prior to his arrest. He would thus not have the guilty knowledge, nor therefore produce P300 in response to the $2000 item, and thus, he would be wrongly cleared of having guilty knowledge. To prevent both types of erroneous decisions, one should test a suspected subject on knowledge of many available, memorable and salient crime details: e.g., the amount of money stolen, the sidearm used to demand the money, the name of the store that was robbed, and so on, up to 6 details in the present example. Thus, as recommended by Rosenfeld et al., (2004), one would run the subject through 6 blocks of trials; each block would probe for knowledge of one kind of detail. Thus the first block could have only members of dollar amount categories, as above. The second block could contain alternative sidearm types; the third block would have only alternative members of store name categories, and so on. Now the binomial theorem may be utilized to calculate the probability of a chance hits on more than one block. For example, there is only a 0.08 probability of a subject hitting on 3 of 6 blocks by chance where there are 5 choices per block. (This probability becomes 0.035 with 7 choices per block.) With 4 of 6 hits with 5 choices per block, the chance probability is 0.015. (The chance probability of a false guilty diagnosis with 7 choices per block is a very low 0.004.) If for n different orthogonally treated items with k choices per item, the subject hits on all n items, the probability of a false positive is 1/k raised to the nth power. (If n<1, the binomial theorem is used to compute the modified chance probability, as above.) This mathematical fact is sometimes referred to as the multiplicative probability principle. The point is that by varying the number of category blocks and choices per block, one can reduce false positive and negative errors to as low a value as one requires—provided (once again) that the guilt assessment within each category is independent of or orthogonal to the assessment in each other category. By isolating category types from one another in separate blocks, as just described, orthogonality is maintained.

It is recalled that because of the noise inherent in EEG recording, a P300 response is always obtained by averaging several trials of a given type; usually the average is based on at least 20, and preferably 30 or more responses. Thus in the examples above, the P300 to P trials is obtained by first averaging all EEG epochs or sweeps associated with P presentations within a given category block. The P300 to I is obtained from an average of some minimally acceptable number of trials, and so on. In the protocol described above, P and I averages are separately obtained for each separate category block, and P-I differences are tested for statistical reliability as in Rosenfeld et al. (2004), and as described above.

Farwell & Donchin (1991, and further expanded in U.S. Pat. Nos. 4,941,477, 363,858, 5,406,956, 5,467,777 to Farwell) and Allen, J., Iacono, W. G. and Danielson, K. D. (1992), The identification of concealed memories using the event-related potential and implicit behavioral measures: A methodology for prediction in the face of individual differences, Psychophysiology, 29, 504-522, hereafter "Allen, et al. (1992)." have utilized a different oddball protocol for using P300 as a recognition index in detection of concealed or guilty knowledge. In these alternative variations of the oddball protocols, the various crime-relevant details are combined within one test block. Thus, in the example above, with a theft of $2000 from a store called "Joe's" involving a 356 magnum sidearm (and so on), within one block there would be the following stimulus set used:

|   | Category | P | T | I1 | I2 | I3 | I4 |
|---|---|---|---|---|---|---|---|
| 1. | dollar amount | $200 | $1000 | $3000 | $4000 | $5000 | $6000 |
| 2. | sidearm | 356 mag | 9 mm | 22 cal | 45 cal | 444 mag | Uzi |
| 3. | Store name | Joe's | Sears | Sam's | Pete's | Saks | Bill's |

(4., 5., 6. are 3 more sets of 6 items in 3 categories; i.e., only half the matrix shown here.)
Note there are P, T, and 4 Is.

Note, there are 6 times 6=36 items, ⅙ of which are different probes, each with p=0.017. Another ⅙ are targets, and the remaining 4/6 are irrelevants. Each item is repeated multiple times (say 12) so that there are 12 times 36 repetitions of all item types, yielding 72 (⅙ of 432) probes per probe average among 4 times as many irrelevants=288 irrelevants per irrelevant average. Likewise there are 72 targets. The method of Farwell & Donchin (1991) established guilt vs. innocence by comparing the cross correlation (an index of similarity; see Rosenfeld et al., 2004) of the P and T waveforms with that of the P and I waveforms. The T was virtually guaranteed to evoke P300 (in a subject attending to the task) because it was rare and required a unique response. If the P300 response to P looked like that to the T, then the subject was diagnosed as possessing and having recognized the guilty knowledge. If the P wave, however, resembled that of the I, then the subject lacked guilty knowledge so that the probe item was just another I-item to this therefore innocent subject. Other methods have been used (e.g., Allen et al., 1992, Rosenfeld et al., 2004) to establish whether or not the P300 for the P was >than that for the I.

As one might have already appreciated, in the above described protocol, all 6 different probes are averaged together, thereby destroying the requisite orthogonality assumption discussed above and in Rosenfeld et al. (2004) and Rosenfeld, J. P. "Brain Fingerprinting:" A Critical Analysis. (2005) in press, Scientific Review of Mental Health Practice, hereafter "Rosenfeld (2005)". To distinguish the 2 protocols so far introduced, we will refer to the one using 1 probe per block as the 1-probe protocol ("1PP") and the one using multiple probes per block as the multiple probe protocol ("MPP"). Although early reports of MPP use suggested accurate diagnosis of innocence and guilt (e.g., Farwell & Donchin, 1991, Allen et al, 1992), more recent studies report poor accuracy (Miyake, Y., Mizutanti, M., & Yamahura, T. (1993) Event Related Potentials as an Indicator of Detecting Information in Field Polygraph Examinations, Polygraph, 22, 131-149, hereafter "Miyake et al., 1993"; Mertens, R., Allen, J. Culp, N., & Crawford, L. (2003), The detection of deception using event-related potentials in a highly realistic mock crime scenario, Psychophysiology, 40, S60 (Poster Abstract), hereafter "Mertens et al., 2003"; Rosenfeld et al., 2004). The 1PP is consistently reported as having high (85-95%) accuracy rates, (e.g., Rosenfeld et al., 2004). Most importantly, the 1PP is on sounder methodological footing since it, and not the MPP, adheres to the orthogonality assumption prerequisite for multiplicative probability computations.

MPP users, could of course, treat each of the 6 probes separately so as to satisfy the orthogonality assumption. However with 72 probe trials using 6 probes, the average for each separate probe would consist of $\frac{1}{6}(72)=12$ trials, a number most would agree to be too small for reliability. The number of total trials could be increased from 432 to 1080 (i.e., multiplying by 2.5) to yield 180 probe trials with 30 trials for each of 6 probes. Then one would have 30 trials per single probe average. At 3 second inter-trial intervals, and allowing for a 50% artifact rejection rate, the total running time would be well over one and a half hours, a great strain on subjects.

U.S. Pat. Nos. 4,941,477; 5,363,858; 5,406,956; and 5,467,777, to Farwell et al and U.S. Pat. Nos. 4,932,416; 5,113,870; 5,170,780; 5,622,181; 5,752,922; 5,846,207; and 5,957,859, to Rosenfeld, as well as other of the publications of Farwell and Rosenfeld cited elsewhere in this disclosure, all disclose discrete probe, target, and irrelevant trials. The Rosenfeld patents disclose the use of P300 amplitude indices as well as scalp amplitude distribution maps to assess P300 phenomena. Also, various procedural protocols are disclosed which vary stimulus types to extend the field of application. The Farwell patents disclose the use of hardware electrode caps and an extended "MERA" or "Mermer" assessment of P300 amplitude (critiqued by Rosenfeld, 2005), and protocols for using P300 as a communication device (of no relevants whatsoever to the present invention). U.S. patent application publication no. 2002-0188217, to Farwell, describes putatively new applications for previously patented technologies, such as in the field of diagnosing Alzheimer's disease, identifying terrorists, and other clinical conditions. Obvious methods for enabling central analysis of remotely collected data are also described. Use of different stimulus modes than those previously used by Farwell are described. Putatively new analytic methods are incorporated, all based on prior art. Also, Farwell describes the use of target stimuli which are relevant rather than irrelevant to a crime. This new feature was also described in Farwell, L. A. & Smith, S. S. (2001), Using Brain MERMER Testing to Detect Knowledge Despite Efforts to Conceal, J. Forensic Sciences, 46 (1), 135-143, hereafter "Farwell & Smith 2001." U.S. patent application publication no. 2003-0032870, to Farwell, describes a method of analyzing spontaneous EEG during interrogation but fails to offer a solution to the prerequisite, key, critical problem of removing speech artifact from the EEG as first identified by Szirtes, J., & Vaughan, H. G., Jr. (1977), Characteristics of cranial and facial potentials associated with speech production, Electroencephalography and Clinical Neurophysiology. 43(3), 386-396 (disclosing continuous recording during ongoing interrogation which is irrelevant to the discrete trials used by the disclosed embodiments). The aspect of this Farwell disclosure which deals with discrete trials is based on the familiar 3-stimulus paradigm used previously by Farwell as detailed above. Finally, U.S. patent application publication no. 2005-0143629 involves combining autonomic as well as EEG physiological indices of cognition (which Rosenfeld, J. P., Alternative views of Bashore and Rapp's (1993) alternatives to traditional polygraphy, Psychological Bulletin, 117, 1995, 159-166, hereafter, "Rosenfeld, 1995," anticipated), again using the familiar 3-stimulus paradigm described above in which test responses are classified as being either indicative or not indicative of known (to the subject) information. An interview component is utilized to help develop stimuli. The disclosed embodiments herein involve neither autonomic variables nor interviews, and do not use the 3-stimulus, 2 classification trial structure.

The disclosed embodiments represent a critical departure in protocol from any of the previous examples of P300-based deception detectors. In the previously discussed, discrete trial protocols of all prior art, separate T (target) trials were utilized to maintain the subject's attention and for some analytic purposes. In the disclosed embodiments, the T trials are combined with P and I trials. Thus in the disclosed embodiments, which we denote as the complex trial (CT) protocol, the beginning of each trial or recording epoch is indicated by the onset of a stimulus which is either a P or an I, which remains on the display terminal for particular time period, for example 1400-1850 ms. (This stimulus duration or "dur" is randomly varying over trials, and the 1400-1850 ms limits may be changed so that both or one is greater or lesser.) At the instant dur expires, the stimulus remains on the screen, but is altered/augmented in some way, which may or may not turn the P or I into a T, i.e., a PT or IT, respectively, combined trial, necessitating the appropriate response from the subject as will be described. In the present example of the CT protocol, let us assume that the initially presented P or I is presented in white font on a black background, and that when dur expires, the stimulus briefly changes to one of 5 colors, and remains on in that color for say 100 additional ms. The subject has been instructed that if the color change is to green, the trial is a target T trial, and the subject should make a "yes" (target) response (e.g., press a button labeled Y). If the color is anything else (e.g., red, blue, yellow), the subject must give a "no" (non-target) response. Our reasoning, borne out by experiments, is that in the CT protocol, the subject must attend even more intensely than in previous 3-stimulus protocols to the probe-irrelevant attribute (i.e., the color change) of the initially presented stimulus, because the target/non-target attribute is brief and its appearance is made unpredictable via the randomly varying property of dur. That is, the subject must keep fixating on the white stimulus, or else he will miss the target/non-target presentation. He is aware, as before, that missed targets and non-targets will betray lack of cooperation with the procedure. By contrast, in previous 3-stimulus protocols with separate target, probe, and irrelevant trials, the subject can allow his attention to wander immediately after stimulus onset, so that he may be less vigilant when the next trial begins.

Figure 2:
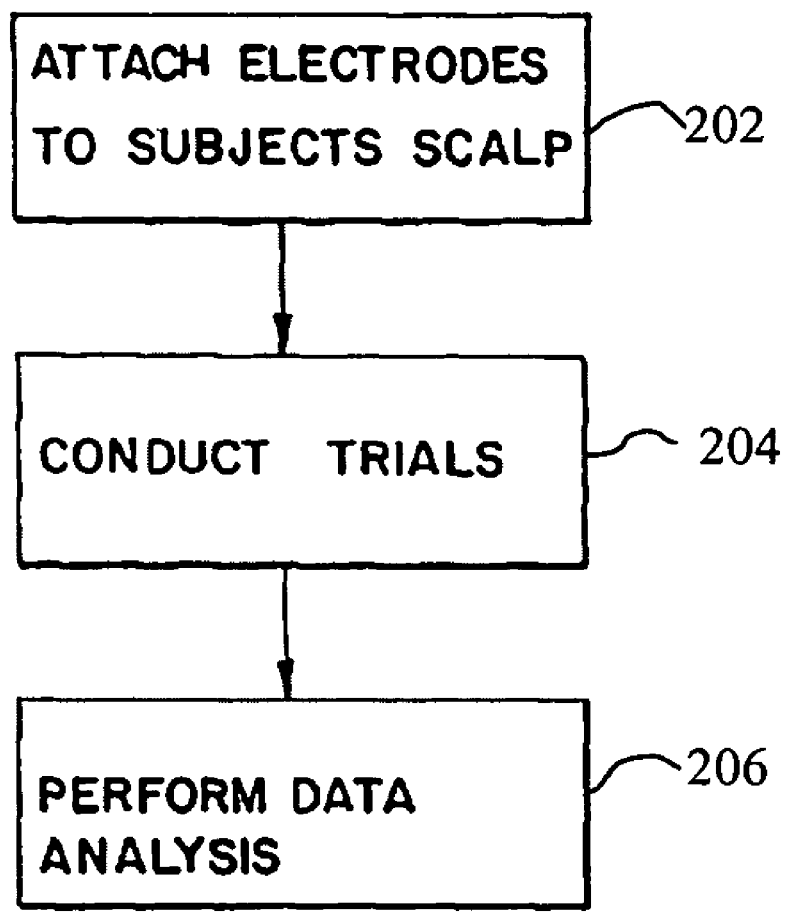
FIG. 2 depicts a flow chart illustrating an exemplary implementation of a deception test according to one embodiment.

Referring to FIG. 2, there is a flow chart 200 illustrating implementation of a deception test according to one embodiment. The embodiment of the deception test involves three steps: First, test equipment is attached to a subject for the purpose of measuring and recording the subject's brain waves (block 202). Next, a series of trials are conducted with the subject while the subject's brain waves are recorded (block 204). Following the series of trials, the brain wave data are analyzed whereby a determination of the subject's status, e.g. familiarity with the subject matter or truthfulness, etc., can be made (block 206).

In particular, one embodiment of a method of inferring deception includes instructing a subject to provide a first acknowledgment of a presentation of an item of a plurality of items, each having a first attribute of a plurality of attributes, provide a second acknowledgement of a presentation of the item having a second attribute of the plurality of attributes, the second attribute being different from the first attribute and provide a third acknowledgement of a presentation of the item having a third attribute of the plurality of attributes, the third attribute being different from the second attribute, the item comprising a subject matter which is comprehensible to the subject independent of the first, second and third attributes, the subject matter characterized by being one of unfamiliar or of questionable familiarity to the subject. In one embodiment, at least a portion of the subject matter may include autobiographical subject matter related to the subject.

In one embodiment, the first acknowledgement includes pressing a first button to generate a first signal, the second acknowledgment includes pressing a second button to generate a second signal and the third acknowledgement includes pressing a third button to generate a third signal. The buttons may be provided on a button-box, mouse or other input device as described herein. As will be described below, other methods of acknowledgement may be utilized.

The subject may be further instructed to provide the first acknowledgement utilizing the subject's non-dominant hand and to provide the second and third acknowledgments utilizing the subject's dominant hand.

The items may include one or more words, dates, pictures or other content. As described, this content is generally categorized as being either unfamiliar to the subject, also referred to as an "irrelevant" or of questionable familiarity to the subject, also referred to as a "probe." As described herein, the disclosed embodiments will allow the determination of whether or not the subject is likely familiar with these questionable items, despite, if relevant, their claims to the contrary. While it cannot be guaranteed that the subject is unfamiliar with the irrelevant items, it will be appreciated that suitable items may be determined. The first, second and third attributes include any visual augmentation of the items, wherein the item is visually presented. For example, these attributes may include colors, e.g. each of the first, second and third attributes are a different color that the item is presented in. Alternatively, where the item includes words or dates, the attributes may include the font, size or typestyle of the presentation. In the case where the item includes words, the attributes may include the letters of the presented word, wherein changing the letters presented changes the meaning of the word, i.e. hate to fate, even where the change results in a non-sensical word, wherein the attribute is the particular letter(s) which is/are varied. In an alternate embodiment, the first and third attributes are identical, i.e. there is no change in the presentation when the attribute is changed from the first to the third attribute.

The method further includes presenting the item to the subject, the presentation having the first attribute. As will be described below, the method may be repeated several times, each repetition being referred to as a trial. In one embodiment, the position of the presentation, e.g. the displayed position on the computer monitor, is varied with each trial.

After the item is presented, the subject, as instructed, is to provide the first acknowledgement, which is received by the system, in response to the presenting.

In one embodiment, the presentation of the item is then maintained with the first attribute for a duration substantially unpredictable by the subject. This duration may range from approximately 1400 to approximately 1850 ms. In an alternative embodiment, such as where the location of presentation is varied, the screen may be erased, i.e. the item presented with the first attribute is cleared from the screen, after a fixed, or alternatively variable, time period. The blank screen is then maintained for the substantially unpredictable duration, as described above.

Upon expiration of the duration, the first attribute is changed to one of the second or third attributes, wherein the third attribute is more likely than the second attribute. In particular, the second attribute should be presented much less frequently than the third attribute. The second attribute is considered the target, as described in more detail below, while the third attribute is considered the non-target. In the embodiment, where the screen is blank, the item is then re-presented having the changed attribute.

Once the attribute has been changed to one of the second or third attributes, and re-presented if necessary, the subject, as instructed, must provide one of the second or third acknowledgments in response to the changing, which are received by the system.

During at least one of the presenting, receiving of the first acknowledgement, maintaining, changing, receiving of one of the second or third acknowledgements, or combinations thereof, at least one brain wave of the subject is recorded. In one embodiment, the at least one brain wave comprises a p300, as was described.

The above process is performed at least once with an item whose subject matter is, or at least assumed to be likely, unfamiliar to the subject, e.g. an "irrelevant," and at least once with an item of questionable familiarity to the subject, e.g. a "probe." It will be appreciated that any ordering of trials, i.e., whether probe trials precedes irrelevant trials or vice versa, may be used and all such permutations of trials are contemplated herein.

Based on the at least one recorded brain waves for each of the at least one irrelevant trial and the at least one probe trial, it can be determined whether the subject has prior familiarity with the subject matter, as described herein. Further, where the subject asserts a claim as to their familiarity with the subject matter of the item, the likely truthfulness of the subject in relation to the claim may also be determined, as described herein.

As will be discussed, the above method is typically repeated multiple times, typically over multiple blocks, each having multiple trials, where the stimulus varied, each block directed to a different category of subject matter.

In an alternate embodiment, the delay from the presenting of the stimulus to the receiving of first acknowledgement may be measured wherein excessive delay indicates the use of counter measures by the subject to thwart the accuracy of the determination of deception. Further, the delay from the changing of the attributes to receiving the second or third acknowledgement maybe measured to indicate whether the subject is properly paying attention or being cooperative. In addition, uncooperativeness may be determined based on receiving the proper acknowledgements the appropriate attributes as instructed.

Figure 3:
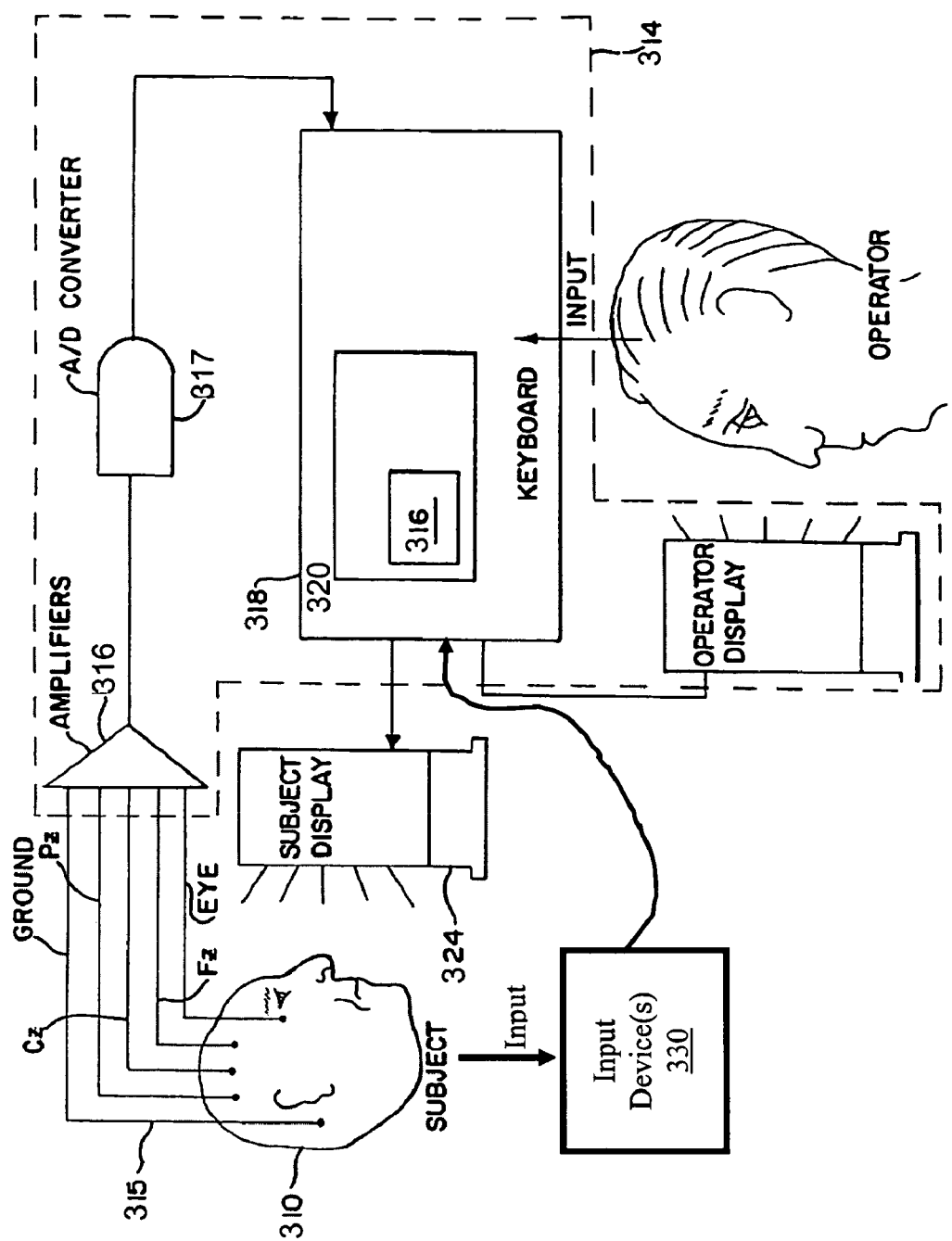
FIG. 3 depicts an exemplary arrangement for connecting a subject to the brain wave measuring and recording equipment for use with the disclosed embodiments.

Referring to FIG. 3, there is illustrated an arrangement for connecting a subject to the brain wave measuring and recording equipment. According to this embodiment, a subject 310 to be tested is coupled with EEG sensing and recording equipment 314. Herein, the phrase "coupled with" is defined to mean directly connected to or indirectly connected through one or more intermediate components. Such intermediate components may include both hardware and software based components. The subject 310 is further provided with one or more input devices 330, coupled with the computer 318, with which to record their responses, i.e.

provide acknowledgements, as described below. The EEG sensing and recording equipment 314 is designed to sense and record the subject's brain waves, in particular P300 type event-related-potentials ("ERP"). Specifically, the subject's Pz, Cz, Fz values are sensed and stored, and the P300 (or P3) response is examined. The recording methods are described in published papers, (see Rosenfeld et al., 2004; Johnson & Rosenfeld, "A new ERP-based deception detector analog II: Utilization of non-selective activation of relevant knowledge", Int. J. Psychophysiology, 12, 289-306, 1992, hereafter "Johnson & Rosenfeld (1992)"), and are also described in U.S. Pat. Nos. 4,932,416 and 5,113,870. The disclosures of these two papers and two patents are specifically incorporated herein by reference.

According to one acceptable method, silver-silver chloride electrodes 315 are attached with conductive EEG paste to Fz, Cz and Pz scalp sites. Linked mastoids are the references with the forehead grounded. Electrodes are also placed supra- and sub-orbitally for EOG recording; i.e., eye movement artifacts occurring during the recording epoch are detected and trials containing 80 μV or higher deflections are discarded and replaced. Signals are amplified 50-100,000 times by Grass P511-K or similar preamplifiers 316 with 3 db filters set to pass signals between 0.1 and 30 Hz. Conditioned signals are led to 12-bit (or more) analog/digital converters 317 sampling one point every 5-10 ms, and then to a microcomputer 18 for on-line analysis and data storage. As explained in more detail below, recording begins approximately 104 milliseconds prior to item presentation and ended 2-3 seconds later as described below. It will be appreciated that other time intervals may be used and may be implementation dependent. Some off-line digital filtering of ERPs is described below. It will be appreciated that the signaling and sampling parameters are implementation dependent and any suitable values may be used.

Once the subject 310 is coupled with the brain wave apparatus 314, the trials portion of the deception test is conducted as described below. In one embodiment, the trials portion of the deception test is conducted utilizing the same computer 318 that used to operate the EEG testing and recording equipment 314, although in alternative embodiments more than one computer may be utilized. In the present embodiment, the computer 318 runs a program 320 that includes the deception test 316 that includes procedures for acquiring and recording the brain wave data, conducting the trials, and analyzing the data. The program 320 that is run on the computer is written in a suitable programming language, such as BASIC, C, or assembly.

For the trials portion of the deception test, a display 324 is utilized. The computer 318 is coupled with the display 324 which is located relative to the subject 310 so that the output of the display 324 is easily observable by the subject 310. The input device(s) 330 may include a mouse, such as a mouse having multiple buttons, or other pointing device, keyboard or a custom input device, such as button box(es) attached to a analog to digital ("A/D") converter interfaced to the computer. It will be appreciated any device(s) suitable to capture the requisite inputs may be used, such as input devices 330 which may be actuated by the subject's 310 fingers, toes, eyes or other appendage. In one embodiment, the computer 318 is an IBM clone however any suitable computer may be used.

In other embodiments, the subject can provide input indirectly by speaking which can actuate a voice-driven relay interface, via an A/D converter, to the computer, or which can be interpreted by the operator who may then operate another device or simply keep score of errors, which, if they exceed 10%, for example, result in a diagnosis of non-cooperation. For example, one method of assuring and enhancing attention to the first stimulus (probe or irrelevant) is to require the subject to repeat it aloud at a variable time after dur expires. The delay is required to prevent artifacts related to speech from distorting the critical first P300 that indexes recognition of the probe. The spoken stimulus repetition will, however, distort the second P300 to the color change (see below), but that latter P300 need not be undistorted: It is not evaluated for purposes of diagnosing probe recognition; in the present embodiment, the second P300 is analogous to an epiphenomenon. That is, it helps to show that the subject reacts to the target, but this may be assumed since it is predicted by voluminous research described above, and we demonstrate the second undistorted P300 to the target below in a research study where no voice was used. The critical response to the target/non-target presentation is behavioral: the subject's correct identification of the target/non-target signaled via the input device(s) 330. Failure to correctly identify at least 90% (for example) of these second stimuli also results in a diagnosis of non-cooperation. Also, as noted elsewhere, the reaction time to the second stimulus is a secondary countermeasure indicator.

Other embodiments which assure the subject's attention to the display and accurate perception of stimuli are possible: 1) Eye-tracking equipment which assures attention to the place on the display screen where stimuli appear, 2)related special cameras which assure correct focus of the subject's eye's lens, 3)alternative presentation methods for first (probe-irrelevant) stimuli: For example, in an alternative embodiment, the original first stimulus (probe/irrelevant) exposure in white may be brief (e.g., 300 ms), and its position in the display screen random and unpredictable. The subject must locate and therefore read this stimulus for it is the eye fixation point for the location of the otherwise unpredictably located second stimulus which comes back (after the variably enduring dur period) in the target or non-target color for 100 ms. It is essential in all embodiments that the stimulus size (e.g., font height and width) be large enough so that partial eye-closure and defocus will not interfere with subject's perception of stimuli. We have found 0.5-0.75 inch height adequate for this purpose in pilot experiments.

Figure 6:
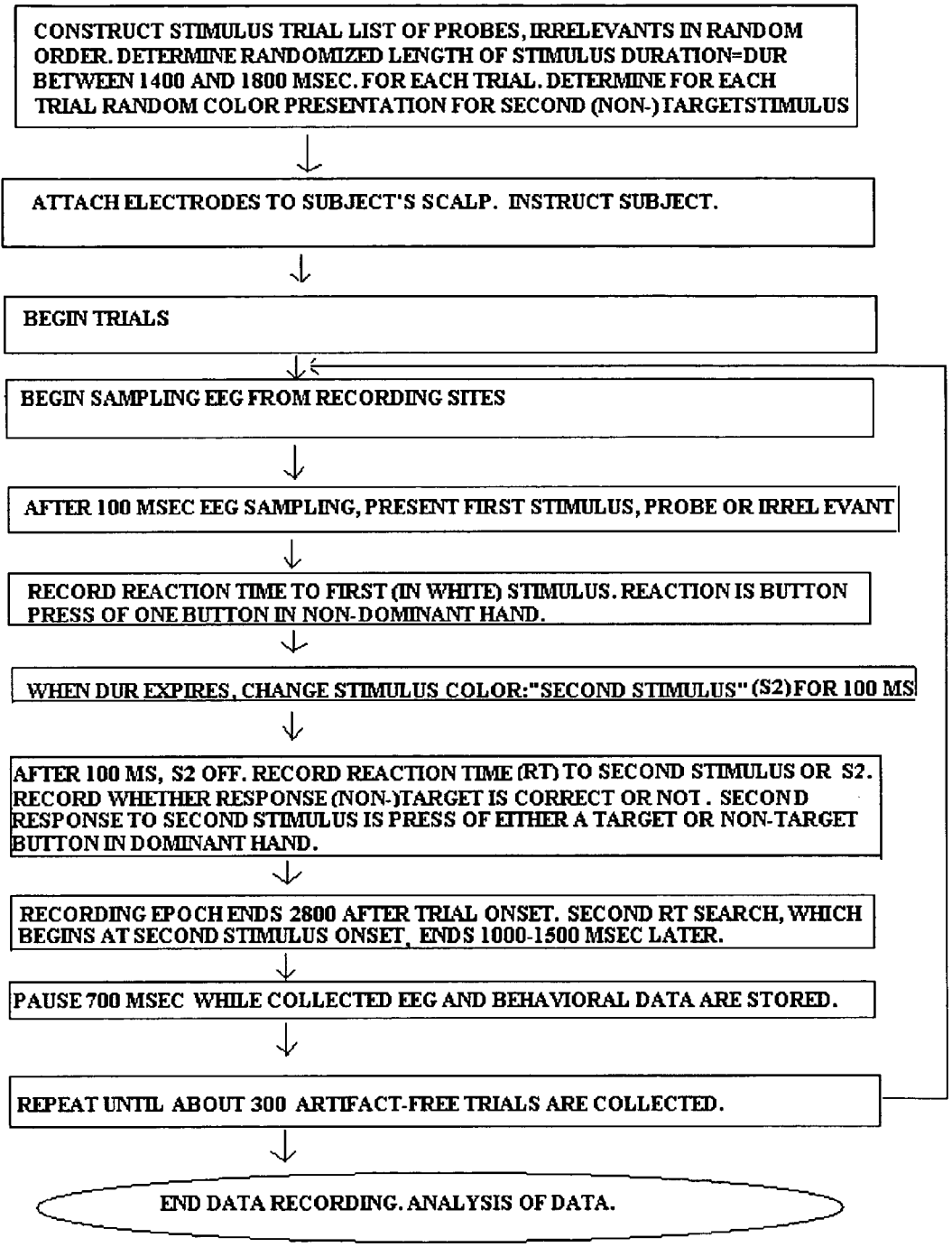
FIG. 6 depicts a flow chart illustrating a deception detection protocol according to one embodiment.

Referring now to FIG. 6, the trials portion of a deception test 316, according to the disclosed embodiments, is composed of a session in which the subject is presented with a series of trials. In one embodiment of the memory test 316, the series of trials may include 3-6 blocks of 200-400 trials each.

On each trial, the first event is the beginning of recording of the EEG from at least one scalp site 315. EEG is recorded for about 100 msec prior to presentation of any stimuli. At the end of this pre-stimulus period, the probe or irrelevant stimulus (S1) is presented in white font on dark background on the display screen 324. (Whether probe or irrelevant is presented is determined by list stored in computer 320 memory after creation prior to test administration). S1 remains on screen for a variable period called "dur" which may randomly vary from 1400-1850 msec. The subject 310 has been pre-instructed (prior to test) to press single button 330 in the non-dominant hand as soon as possible after onset of S1 so as to indicate his perception of S1, whether probe or irrelevant. The next event is the computer storage of the reaction time (time from S1 onset to button press). (Significant (e.g., >10%) numbers of missing button presses within about 1000 msec from S1 onset indicate non-cooperative subject. Excessively long reaction times indicate countermeasure usage.) When "dur" expires, the stimulus color changes to one of many (e.g., 5) colors (e.g., red, green, blue, yellow, purple). The color change defines the second stimulus (S2) and if the color change is to green, the S2 is considered to be a target, as defined for the subject prior to test. All other color changes are considered to be non-targets. S2 lasts for about 100 ms. The aim is to have it clearly supraliminal, but otherwise as brief as possible. S2 exposure time will depend on display 324 brightness. The subject 310 has been instructed prior to the test to press a target button on a button box 330 located in his dominant hand if the S2 was a change to green, and another, non-target button if the S2 color change was not to green. The subject has been instructed prior to the test to press in response to S2 as soon as possible. The computer 320 begins looking for S2 reaction time at S2 onset and continues looking for about 1000-1500 msec thereafter. It records reaction time and correctness of response. EEG data collection stops at 2800 msec after S1 onset. An additional 700 msec passes prior to next trial onset. Depending on how long the search for the S2 reaction time is allowed to continue, the search may continue for a brief time after EEG data collection ends for the trial It should be appreciated that the color change method is just one example of how the CT protocol can be implemented. Other examples: the stimulus can come on in white and when dur expires, 1) a dot is presented either to the left or right of the stimulus, the latter being the target, 2)the stimulus is either underlined or over-lined, with one of these two alterations designated as the target, 3) the stimulus is either circled or squared, with one of these two changes designated as the target, 4) one letter of the stimulus changes. The subject is instructed that if it changes to a defined letter, this is a target, other letter changes are non-targets, and so on.

The CT paradigm of the disclosed embodiments will overcome serious vulnerabilities of both the 1PP and MPP protocols: 1) Most seriously, Rosenfeld et al., (2004) demonstrated that both 3 stimulus protocols are vulnerable to countermeasures (CMs). That is, subjects may be taught to generate various covert responses on I trials, and these enhance the size of the P300 to I, since the I's are thereby converted to covert targets. Moreover, the multiple response demands generate a dual task effect, reducing the P300s to probes (Kramer, A. F., Sirevaag, E. J., & Braune, R., A psychological assessment of operator workload during simulated flight missions, Human Factors, 29(2), 145-160, hereafter "Kramer et al., 1987"). The separately presented targets were largely unaffected. The ultimate effect was reduction of the P-I difference such that detection of deception rate was reduced to 50% of the cases (down from 90%) in the 1PP, or to 18% (from 82%) in the MPP. 2) The 1PP and MPP protocols are very sensitive to autobiographical or over-learned material, but not so sensitive to incidentally learned details of a crime (Rosenfeld, J. P., Biroschak, J. R., & Furedy, J. J., (2005) in press, P300-based detection of concealed autobiographical versus incidentally acquired information in target and non-target paradigms, Int. J. Psychophysiology, 2005, hereafter "Rosenfeld et al., 2005b"). 3) Rosenfeld et al. (2004) demonstrated that having learned CMs on one occasion, a subject may cease to use them on a second occasion, yet the P300-based hit rate remains low (58%). It was verified that the CMs were not used on the second occasion because reaction time ("RT") to I stimuli was normal on the second occasion, it having been previously established that when subjects explicitly used CMs on I trials, the entire I-trial RT distribution over subjects was shifted up and out of the normal range. I.e., RT could be used as an index of CM use on the first occasion with explicit CM use, but not in the second occasion when the detection rate was still a low 58%.

With increased attentional demands in the CT protocol of the disclosed embodiments, CMs will be less effective nor will there be such serious carryover effects on later occasions. It is also expected that incidentally learned information will be more readily detected since the CT method forces intensified attention to and therefore deeper processing of stimuli. In an alternate embodiment, a method of combining pictures with verbal labeling of incidentally acquired crime details in presenting P and I stimuli is added, to aid in recall of incidentally learned information shown by Rosenfeld, et al. (2005b) to be less memorable than autobiographical information with prior detection methods. In this embodiment, the spelled out name of the test item has an associated photograph, e.g. picture of the stolen ring, that is also displayed on the screen which the subject views.

It should be added that in one embodiment, in addition to the target/non-target button press which comes after dur expires and indicates the subject's decision about target/non-target, we also require subjects to press one button (always the same) immediately after the stimulus is presented. In that way, RT to stimulus onset may be used as a CM detector as in Rosenfeld et al., (2004). We will also have RT to the color change, timed from the onset of the color change, which will also indicate degree of cooperation with the target discrimination task.

While the measuring reaction time as an adjunct measure of deception is known, in the disclosed embodiments, RT is used as an indicator of countermeasure use. In the disclosed embodiments, the RT of the subject to acknowledge the initial stimulus presentation is used do determine if the subject is utilizing countermeasures while the RT of the subject to acknowledge the target-non-target transition is used to determine the subject's attentiveness which forces the subject's attention to probes or, failing that, forces a diagnosis of non-cooperation with the task, if the target identification rate is poor.

Experiment 1: In the following example of the novel CT protocol, 12 guilty subjects were run with the color change procedure described above with the following stimuli:

| STIMULUS TYPE | NUMBER | PROBABILITY |
| --- | --- | --- |
| Probe Target (PT) | 30 | .9 |
| Probe non-Target (PN) | 30 | .9 |
| Irrelevant Target (IT) | 30 | .9 |
| Irrelevant non-Target (IN) | 240 | .73 |
| All Probes | 60 | .18 |

Note,
PT means a probe which changes to a target color.
PN means a probe changing to a non-target color.
An IT is an I changing to a target color,
and an IN is an I changing to a non-target color.

Note, PT means a probe which changes to a target color. PN means a probe changing to a non-target color. An IT is an I changing to a target color, and an IN is an I changing to a non-target color.

Figure 4:
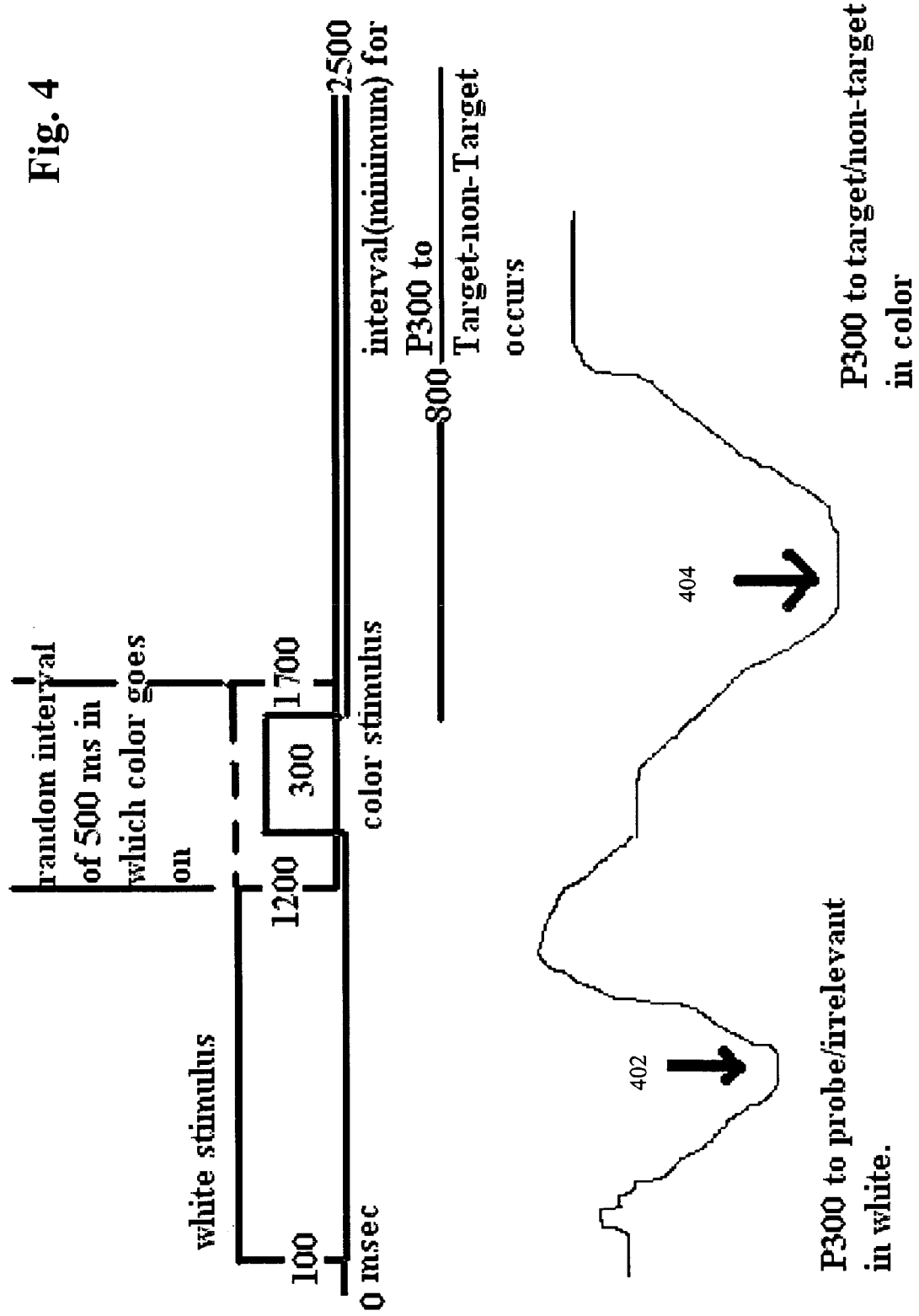
FIG. 4 illustrates the trial structure for a pilot experiment according to the disclosed embodiments.

The basic 1-probe per block protocol (1PP) was utilized on just 1 block. The category of information for all stimuli were dates. For each subject, the P was that subject's birth date, and the irrelevant (I) trials were other meaningless dates. The trial structure for this pilot experiment is given in FIG. 4 (with some duration values somewhat different than previously suggested in a more preferred embodiment), and under it is the hypothetical ERP recording obtained from the Pz site on scalp expected for PT trials.

It is noted that two P300s are expected on this PT trial, the first 402, in response to the probe presentation and the second 404, in response to the target presentation. One expects a much smaller second P300 on PN and IN trials than on PT and IT trials, since target events (PT and IT), not non-target events (PN and IN), evoke P300. Actually obtained results are shown in FIG. 5.

Figure 5:
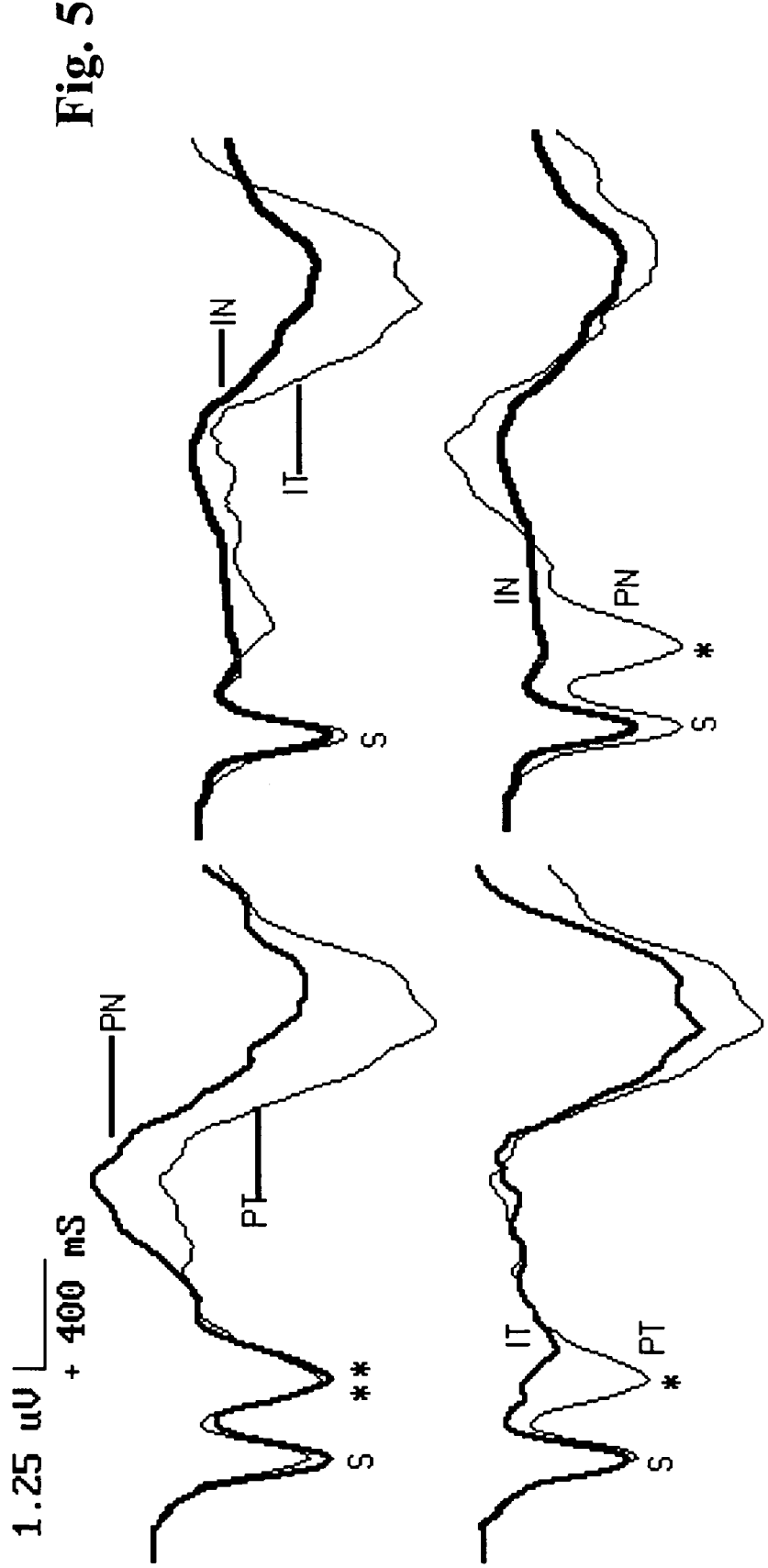
FIG. 5 depicts the results obtained from the experiment depicted in FIG. 4.

These results, as shown in FIG. 5, are grand average EEG epochs (sweeps) of 2560 ms duration from the first 10 of 12 subjects run, sorted by trial type and superimposed to illustrate various attributes: Note all sweeps have an early downgoing positive wave labeled "S". This stands for Sensory Evoked Potential, and is the rapid response of the brain to the light (from the stimulus) impinging on the retina. S does not discriminate trial types of interest here. Trials with "P" (PT and PN) are probe trials and show early P300 responses indicated with asterisks. In the upper left, both (thus 2 asterisks) superimposed PT and PN trials have P300s in response to recognition of the probe(P). The PT, however, has a large P300 to the target which has a delayed presentation and thus a late P300. (The PN also has a late P300 of much reduced size since there was no target color change.) In the superimposed pair of waveforms in the lower left, the PT but not the IT has the early P300 indicating recognition, but note that both waves have comparably large late target P300s as both are from target trials. Likewise, the IN and IT waves in the panels on the right lack the early P300 seen in the PN wave at the lower right. Note that both PN and PT waves have early probe-elicited P300s and are clearly visible in the superimpositions on IN and IT, respectively, shown in the lower left and right panels.

The late target evoked P300s were expected in both I and P target trials, and help to illustrate that targets were attended, as cooperation with the task requires. The actual behavioral correct response rates provide a more quantitative index of this cooperation. (Less than 90% correct responses is usually taken to indicate less than acceptable cooperation. The value of this parameter may be variable, depending upon the needs of the investigator.) These late target responses are broader than the early P300s because the color changes evoking the late P300s occur at random times in the later parts of the epoch, and thus elicit P300s of variable latencies which average to a broader waveform. They are large because of the required unique behavioral response. They are undoubtedly P300s since besides having the correct positive polarity and latency range (400-800 ms post stimulus), they were largest at the Pz sites shown above and smallest at Fz sites (not shown here), i.e., they show the classic P300 scalp distribution (Fabiani et al., 1987).

In using the bootstrapped amplitude difference tests to assess peak-peak P—I differences within individuals (as in Rosenfeld et al., 2004), 11/12 (92%) of these subjects were correctly identified. (All P300s to probes, PT and PN (about 60 responses on average), were compared to a randomly selected 60 irrelevant P300s). These subjects were taught countermeasures on a second occasion (as in Rosenfeld et al., 2004). The detection accuracy rate remained high at 83% (10/11).

It is added that although I have used just 3 sites in exemplar studies of the new protocol introduced here, with P300 amplitude analysis on one site, it is possible to use up to 256 electrodes in conjunction with the present novel CT protocol. One could combine data from these sites using multiple regression and related methods or the Virtual Site methods described in Appendix 1 below. One could also use scalp distribution as a dependent variable in addition to amplitude, as described in U.S. Pat. No. 5,957,859 and in the material in Appendix 1 below, excerpted from Rosenfeld, J. P. Scaled P300 Scalp Profiles in Detection of Deception September 2002, Report No. (DoDPI02-R-0005). Department of Defense Polygraph Institute, Fort Jackson, S.C. 29207-5000. DTIC No. ADA407107.

It is also the case that although the examples of concealed information detection presented above involve crimes, the CT protocol herein disclosed can be used to detect any kind of concealed information in any situation, e.g., the situation of a litigating malingerer claiming to not recall autobiographical or recently learned information.

It is also noted that although we have described one method of assessing P300 amplitude, other known methods may also be used: e.g., using single point peaks for base-peak as well as peak-peak measures; using areas under P300 components measured for longer times than those described above for both base-peak, as well as peak-peak methods; and so on. Also, as noted above, other methods of measuring brain activity are possible with the disclosed CT paradigm. For example, a magnetoencephalogram (MeG) may be utilized which records P300 expressed as a function of the magnetic fields associated with EEG voltages, and thereby provides a measure of P300 where no contact with the subject's skin is involved. Other brain activity indices, e.g., fMRI, PET, etc, are also possible to use with the disclosed CT paradigm described herein.

It is therefore intended that the foregoing detailed description be regarded as illustrative rather than limiting, and that it be understood that it is the following claims, including all equivalents, that are intended to define the spirit and scope of this invention.

APPENDIX 1

In recent years we have studied the P300 profile or amplitude distribution across the scalp—an "isovoltic" brain map—as an index of deception using mostly GKT analogues. Johnson (1988, 1993) has given elegant theoretical accounts of the significance of varying scalp profiles in which he emphases that each particular profile represents a unique pattern of activation of P3 neurogenerating neurons associated with a particular psychological state or task. Thus if two tasks or conditions, within or between subjects, produce differing amplitude distributions (or profiles), one may infer that differentially located groups of P3-neurogenerating neurons are involved by the two conditions. Although there are other explanations for differing profiles (e.g. Donchin, Spencer, & Dien, 1997), all are consistent in assuming that differing profiles in two states means that the brain is working differently in the two states. The profiles are actually scaled scalp distributions, the scaling being necessary to guarantee that the scaled amplitude profiles are orthogonal to simple amplitude differences (McCarthy & Wood, 1985; Johnson, 1988, 1993). The typical familiar statistical method of showing that two group profiles differ at the same n sites is to do a 2 (groups or conditions)-by- n (sites) ANOVA on the scaled amplitudes and show a significant group by-site interaction.

We have thus recently utilized the scalp profile as another brain wave indicator of the two states of deception versus truth-telling. One of our first studies (Rosenfeld et al. 1999) along this line involved the use of a match-to-sample paradigm with nine probes. In this paradigm, a 3 digit (sample) number is presented on the screen and removed. A few seconds later a probe number is presented and the subject must decide whether or not the probe matches the sample. Of the nine probes presented prior to the next sample, there is only one match. There were two groups of subjects: liars (L) and truth-tellers (T). The T-subjects were told to do their best on the easy test, and that they would probably score 100% correct. The L-subjects were manipulated to score 50% correct on both matches (MAT) and mismatches (MIS). Thus for T-subjects there were two possible stimulus-responses combinations: 1) Match stimulus and Match response (Mat-Mat), 2) Mismatch stimulus and Mismatch response (Mis-Mis). For the L-subjects there were two additional possible combinations, Mat-Mis and Mis-Mat on dishonest trials. One major finding was that a comparison of T and L subjects' scaled P3 amplitudes as a function of site (Fz, Pz, Cz) and stimulus type (regardless of response) yielded a significant group-by-site interaction, meaning that the P3 profiles of the truth group differed from those of the liar group. Both the Mat and especially the Mis profiles of the liar group showed a quadratic component, whereas the T-profiles appear more linear (or, as we jest in the lab, "liars are crooked.")

The other major finding of this study was that within just the liars, regardless of the stimulus type, the profiles superimposed, suggesting a deception-specific profile. In the truthtellers, the two corresponding profiles clearly differed, as they should have, since the brain probably does process matches differently than mismatches and thus the associated neurogenerator sets recruited by the two kinds of processing should be different. However, engaging in deception appears to swamp out these effects, as just noted.

As the results just described were being collected, we were prompted to re-analyze profile data from some older published studies in which we had the profile data set but analyzed it only for simple amplitude and latency effects at one site only. One study utilized an autobiographical oddball paradigm with subjects' birthdates as oddballs. The other study utilized a match-to-sample paradigm with one test probe per sample. In each study, there were two conditions, a truth-telling condition and a lie condition in which subjects were instructed to lie on about 50% of the trials. The key results (from Rosenfeld et al., 1998) were that if one looked only at the truth conditions in both studies there was a clear interaction (statistically confirmed) between the autobiographical and match-to-sample studies. This was quite expectable since the two paradigms have obvious differences, requiring differential cognitive processes which should activate differentially located sets of neurogenerator neurons, a situation resulting (see above) in differing scalp profiles. In contrast, the profiles from the two paradigms in the lie conditions yielded no significant interaction and were indeed virtually superimposed. Again, there seemed to be a deception-specific profile which seemed to swamp out other influences which could express their effects in truth-tellers.

In another study (Miller, 1999a; Miller et. al., 2002) using an autobiographical paradigm, two groups of subjects, truth-tellers (T) and liars (L), were run in two blocks each. In the first, the autobiographical oddball stimulus was the subject's phone number, and all subjects were instructed to respond truthfully. In the second block where the oddball was the birth date, the T-subjects responded truthfully, whereas the L-group lied on 50% of the trials. We did this so as to be able to compare honest and deceptive ERP responses. The results were that only liars had a P3 profile which differed from the others (all truth-telling blocks), an effect which was statistically confirmed. When the lie and truth response trials were separately plotted for the L-group, however (from Miller 1999a; Miller et al., 2002), no interaction appeared nor was found statistically. Again, it appeared that within the liar group, the deceptive mind-set from lie trials carried over in truth-telling trials, swamping out the effect of the specific behavioral response of either truthful or deceptive.

Most recently, we have been able in two studies to obtain response-specific profiles during 50% lie blocks (Miller, 1999b, Rosenfeld, Rao, Soskins, & Miller, 2002). In the first of these studies (Miller, 1999b), a novel feature was the addition of four different recording sites on the scalp to add to the three midline sites (Fz, Cz, Pz) we used previously in all studies. In the other study (Rosenfeld et al., 2002), we utilized verbal responding, rather than button-pressing. We believe it was important for us to have shown that it was ultimately possible to observe different profiles for honest and dishonest trials within one trial block for both theoretical and practical reasons: theoretically, this demonstration even more strongly supports the notion that the profile measure may be a direct index of deception. (This is discussed fully in Rosenfeld et al., 2002.) The good theoretical point turns out to have an important practical implication: if there is a direct index of deception, one need not infer deception from the inconsistency of P300 amplitude and behavioral response as one does in the paradigm in which P300 amplitude at one site is used as indirect recognition index and thus deception indicator (e.g., Farwell & Donchin, 1991; Rosenfeld et al., 1988). In the latter, older approach—as with all GKT approaches—unless the testmaker goes to the extreme lengths suggested by Lykken (1981, pp. 257-296) in development of the GKT, which few testmakers are willing or able to do (accounting for the unpopularity of GKTs in the deception detection community), then the absence of a P300 in a guilty person to a relevant item may falsely indicate innocence when the simple truth is that the stimulus item was never noticed or forgotten by the perpetrator. Even more practically, in the type of screening analog which we report on here, it becomes possible to compare responses to various items within a trial block, some of which are answered truthfully, some falsely.

In view of the forgoing, we here attempted to develop a deception detection test based on the P300 profile. The work described below goes well beyond what we have previously reported: 1) We utilized 30 scalp recording sites in the hope of sampling the brain with finer resolution than in our previous work which utilized 3-7 sites. 2) We developed completely novel statistical tests designed to be utilized within subjects to determine innocence or guilt. All results previously presented regarding profile were based on standard group analysis methods. Moreover, the individual bootstrap tests utilized in the earlier GKT-type paradigms are designed to answer the simple question: is the P300 at Pz in case A larger than that in case B? Our newer approach, in contrast, asks: is the profile shape across 30 sites different in deceptive vs. honest conditions? This is a much more complex undertaking and required altogether novel (and commercially unavailable) software. 3) In fact, although all 30 sites were utilized for initial recording, we appreciated (based on Donchin et al., 1997) that there would be redundancy in clusters of correlated sites, and so prior to utilizing the individual diagnostic software, a Principal Component Analysis (PCA) was performed on the set of ERP averages from all sites in all subjects in all conditions. The point of this analysis was to determine a group of spatial components or "virtual sites," each composed of highly correlated real sites which would allow a more efficient application of the diagnostic tests. This is because the PCA reduces the number of points in all analyzed profiles, and incorporates presumably, only the meaningful areas (and their component sites) where deception-relevant activity is present. This is a practical matter, since it should yield more reliable, valid, and accurate detection. Theoretically, identifying these deception-relevant areas gives us an idea of where on the scalp deception-related brain activity is manifest. One cannot generalize from scalp to brain location with great accuracy, but identification of deception-relevant scalp areas gives us a preliminary, if crude idea of what the deception-relevant brain areas are.

Methods

Subjects: The 23 subjects reported on here (15 males) were drawn from the introductory psychology course pool at Northwestern University. All had normal or corrected vision (but no contact lenses were permitted). All participated in the research as a fulfillment of a course requirement. Initially, 48 subjects were recruited. Table 4 tabulates the reasons for attrition to the final 23.

TABLE 4

Use of 48 Subjects

| Good Files: | |
| --- | --- |
| Innocent subjects | 7 |
| Guilty of one act | 7 |
| Guilty of two acts | 9 |
| Total | 23 |
| Bad Files: | |
| Dismissed due to outside construction noise | 5 |
| Data lost due to computer crashes | 6 |
| Data dropped due to excessive blinking | 2 |
| Data dropped due to sleeping in run | 2 |
| Data dropped due to high electrode impedance | 2 |
| Data dropped due to excessive head size | 1 |
| Data dropped due to excessive coughing | 1 |
| Data dropped due to guilt on 5 items | 1 |
| No-shows or would not complete experiment | 5 |

(It is noted that over 100 subjects were run previous to the 48 tabulated here. Many were put through a pilot study using an autobiographical oddball paradigm and using 15 sites. These subjects were run to allow us to validate our analysis software.

Procedures

Subjects entered the laboratory and were informed about the nature of the experiment, and then signed a consent form. An electrocap was now applied with 30 electrodes. (Two other electrodes were used to monitor EOG). Our impedance criterion was 5 kohms. The subjects were then shown a list of eight antisocial or illegal acts to study as an audiotape of those acts was played. The acts on the list were two-word phrases, such as 'smoked pot,' and the full meaning of the phrase was explained on the tape, e.g. "The phrase "smoked pot" means that you have smoked marijuana at least once a week for a three or more month period at some time in the past five years." After hearing the meanings of the phrases, the subjects read aloud sentences both admitting and denying the acts. The aim of this was non-selective activation of their memories of their actual acts, as in Johnson & Rosenfeld (1992). The subjects were led to believe we were recording brain activity during the activation phase (we were not), so that just between it and the real recording period we could make the following mock accusation: "We think you did A but possibly also B, C, or D." Of acts A-D—selected to be of moderate probability in our population based on much previous study—we would compare ERPs associated with control (accused innocent) acts with those profiles associated with relevant (accused guilty) acts. The subject then was led into the recording room where the stimuli were presented on a display screen 1 m before them. Stimulus items (the 2-word phrases) were presented one at a time every 5 sec. After the recording session, the subject was led to a private room and allowed to shut the door, leaving him/her alone. Next to each phrase on a fresh two-phrase list, were yes and no blank lines. The subjects were told to check one line (yes or no) according to their best memory. They had been led to believe that they were alone in the room and that they could keep the list on them to dispose of as they pleased later. In fact, a closed circuit television system with a concealed camera recorded the list during line checking. (Subjects were later debriefed about this and all procedures as approved by the Northwestern IRB.) The system did not record on tape or anywhere else what the subject checked. It simply carried the signal via cable to a closed circuit TV monitor observed in a neighboring room by an experimenter. Only the list was shown. No identifying information was stored. This was our method of obtaining ground truth.

The trial structure was as follows: The trial began with pre-stimulus ERP recording for 104 ms. At 104 ms, at random, one of nine two-word phrases was presented, centered above a fixation point. Eight of these were the phrases seen earlier by the subject. A novel phrase was "Lie Test." We had explained to the subject prior to running that this phrase would be presented and that it meant "you are taking a lie-detector test, which you really are, so you must press this yes button when you see this phrase. Since you want to appear of good character, you will press the no-button to the other phrases even though you may be lying to one or more of them when you do. We want to see if our brain-wave lie-detector can catch you." The subjects rested their right hands on a box containing yes and no-buttons, and responded with index finger presses as appropriate. The stimulus remained on for 1296 ms and the recording continued until 2048 ms. Immediately following the end of the recording epoch, the message "Respond" appeared and lasted 1.5 s. The response had to occur in that window, or the trial was rejected. After it expired, another 1.5 period of no events occurred prior to start of the next trial. The total inter-trial (inter-stimulus) interval was thus 5 s.

EEG Methods, Data Processing

Figure 7:
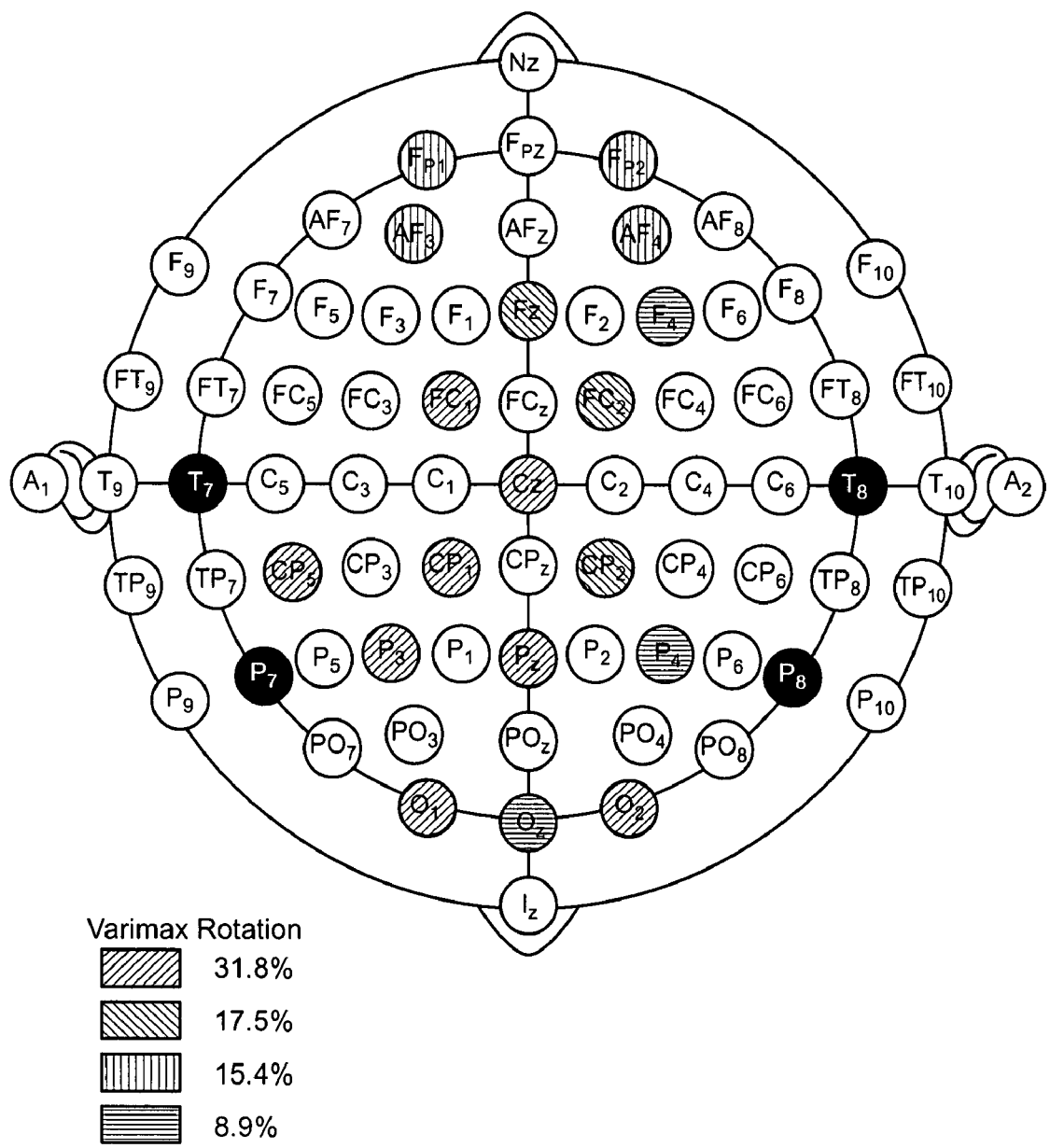
FIG. 7 depicts an exemplary components derived from principal component analysis in space of scalp surface with varimax rotation.

Thirty electrodes in an electrocap were applied as shown in FIG. 7, based on Pivik, Broughton, Copolla, Davidson, Fox, & Nuwer, (1993). (This figure shows all sites in Pivik et al., 1993. We used only a subset of 30 including those with colors filled in, which indicate component loadings as described below.) The electrocap leads were led to a 32-channel amplifier system from Contact Precision Instruments. The nose was the reference and the forehead was grounded. The amplifiers passed signals from 0.3 to 30 Hz and amplified them by a factor of 50,000. The outputs were led to a 12-bit Keithley-Metrobyte A/D converter sampling at 125 Hz, which was connected to a Pentium II computer running at 500 MHz. The software was designed to record EEG while presenting stimuli and controlling all aspects of the experiment. After a run of 256 trials, single sweeps were averaged, filtered and compressed for storage on a Castlewood ORB drive. Averages were stored for display as well as for use in a principal component analysis (PCA). The averages to each of the nine stimuli were separately stored, and the filtered single sweeps (3 db point=4.23 Hz) for all trials, appropriately coded for stimulus and response, were stored.

As in the countermeasures studies described above, EOG was differentially recorded from two electrodes above and below the right eye. They were not one above the other, but diagonally placed so as to pick up both vertical and horizontal eye movements as confirmed in pilot studies. The on-line artifact rejection criterion was 80 uV.

Both stored single sweeps and averages were exported as text files into SCAN 4.11 (Neuroscan Corp). Ocular and other artifacts were removed with SCAN's ocular artifact removal and linear detrending transforms. Then, we visually inspected single sweeps on all files and hand-removed suspicious sweeps, (about 15 per subject). The artifacted averages were then exported to SYSTAT 8.0 (SPSS Co.) where a PCA was performed on 28 of the 30 electrodes. It was decided to drop sites T 7 and F 8 as these lateral sites were found to be quite noisy in several subjects. (This was probably due to flaw either in our electrocap application technique or in the electrocap.) Thus the data matrix input to the PCA consisted of 28 electrode sites by 14,490 observations (70 timepoints X 9 stimulus types X 23 subjects).

The purpose of the PCA in space was to tell us how to use the data from the 28 sites actually recorded. That is, the PCA tells us which sites contain mutually redundant information. All these can be put into a cluster or virtual site containing information from its component sites which the PCA also shows to be good representations of a common factor or component. The PCA provides that information by outputting a set of "loadings" for all recorded sites. Only some of the actual sites will load highly on (i.e., represent strongly) a given factor.

Once we completed the spatial PCA, we computed virtual ERP single sweeps which are weighted averages of site values within spatial clusters. We then performed statistical analyses (described below) on each subject using bootstrapped cross-correlations and ANOVAs. These involve many interactions and are very time consuming (even on a 1.7 GHz Pentium 4 which we used for iterative analysis). Thus, once a PCA is run, its results shape the analyses on all subjects. It took 2 weeks to do the PCA and intra-subject analyses on 23 subjects. Actually, 2 PCAs were run, one with a varimax rotation and another with an oblimin rotation, (as suggested by reviewers of first draft of this report).

Figure 8:
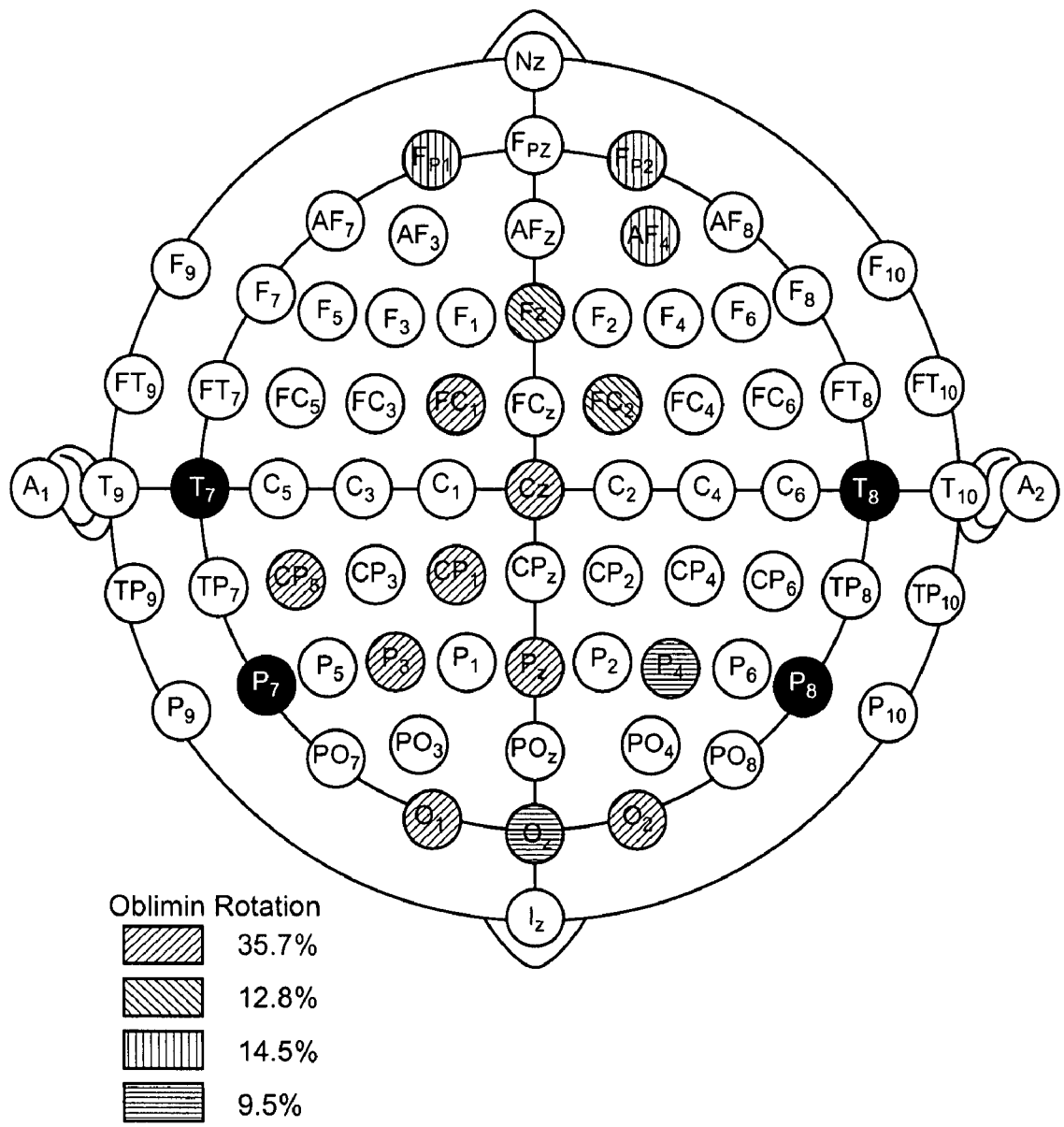
FIG. 8 depicts alternate exemplary components derived from principal component analysis in space of scalp surface with oblimin rotation.
Figure 9:
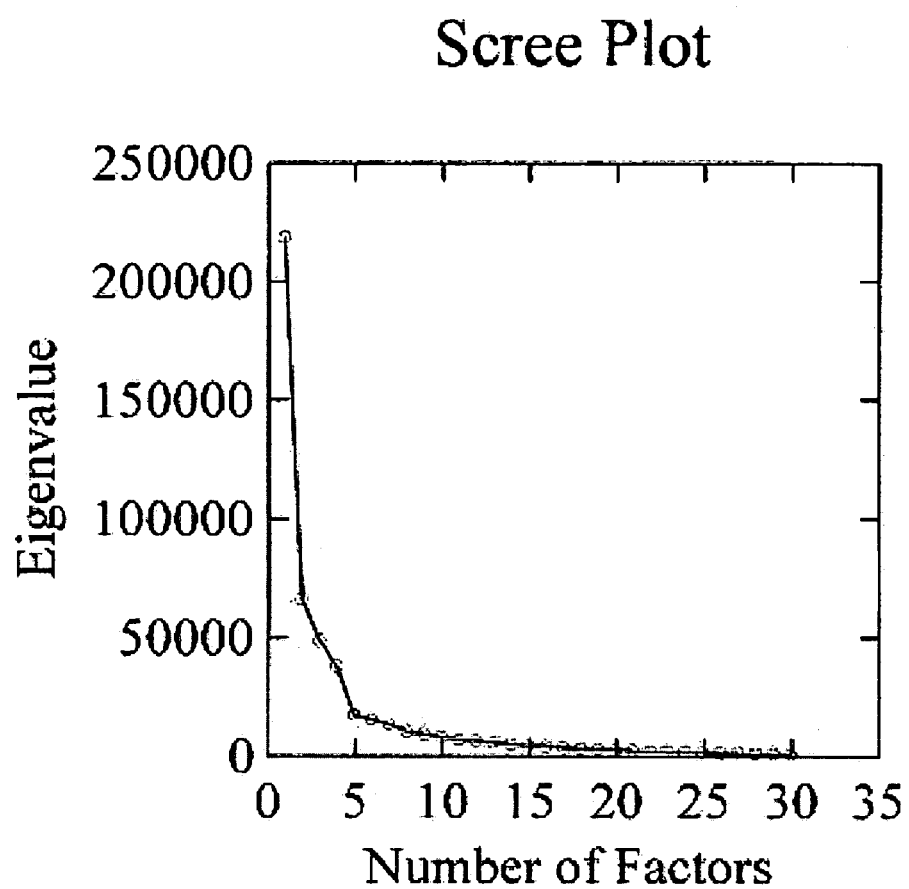
FIG. 9 depicts a plot of eigenvalue as a f (factor number) for the presently submitted dataset.

There were basic choices to be made in terms of how to run the PCA: How many factors (virtual sites) should be used? What should be the criterion for dropping real sites from virtual clusters? Should sites within a cluster be weighted (multiplied) by respective loadings, or by 1.0? The component loadings are shown in FIG. 7 (varimax orthogonal rotation) and FIG. 8 (oblimin non-orthogonal rotation). As the outputs of both rotations looked similar (and substantially different from the PCA outputs submitted prior to the first peer review, we chose to use the orthogonal rotation, as initially proposed, and as is typically used by ERP workers. Table 5 lists the 30 sites used in the study and the virtual sites on which they loaded significantly, if any. Specifically, we chose for this report to go with 4 factors or virtual sites. This decision was based on PCAs, and most especially by the Scree Plot Test (Catell, 1966) results. This plot of eigenvalue as a f (factor number) for the presently submitted dataset is shown in FIG. 9 for the oblimin rotation; the varimax was similar. This plots essentially the amount of variance in the data accounted for by the various factors from 1 to 28 (the number of sites/variables). It is seen that there is one key factor with eigenvalue >200,000. There appeared to our eyes to be three more real factors, after which all points seemed to be on the same trend line. Our PCA on four factors accounted for about 74% of total variance, clearly a sizeable amount according to our factor analysis consultants. These four factors accounted for about 31.8% (factor 1), 17.5% (factor 2), 15.4% (factor 3), and 8.9% (factor 4) of variance, respectively. Other PCAs loading sets, using different numbers of factors were done. These were covariance-based PCAs. Of course, the more factors one uses, the greater the total amount of variance accounted for, but there is a point of diminishing returns: where there are no further inflection points in the Scree Plot. We utilized a correlation matrix PCA to obtain standardized rotated loadings for each of four factors. We then decided to retain all sites with loadings of 0.5 or more (in a 0 to 1.0 range). This is a compromise choice, as with the number of factors. Thus for each of the four components (factors) we identified, all sites showing loadings of 0.5 or more were simply averaged to give us a value for the virtual site (cluster or factor). We might have chosen to use a weighted average, with each site value multiplied by its respective loading, but we reasoned that such loadings differences (given our 0.5 cutoff) could be due to chance and our results would then not generalize to other datasets. Table 5 shows the loadings of sites on factors.

FIG. 7 suggests four areas on the scalp where clusters exist. Virtual site or Cluster #1 (green sites) has a large central-parietal contribution. Cluster #2 (blue sites) appears frontal. Cluster #3 appears right frontal-central, and Cluster #4 involves frontal F4 to P4 to OZ. For each real site within a cluster, the filtered single sweeps for each real site were converted to a set of filtered single sweeps for virtual sites by averaging the real site values into one virtual site value for each time point in the single sweeps. Now we proceeded to compare scalp distributions, scaled and unscaled, across comparisons of interest, e.g., control vs. relevant distributions within innocent and guilty individuals. To compare scaled scalp distributions, we used a modification of the method of Srebro (1996). This method basically asks if there is a cross-correlation across the two plots (e.g., control and relevant) of scalp amplitude as a function of virtual site for the two item types. The use of the Pearson Correlation Function accomplishes the scaling. In our novel approach, we randomly selected with replacement a sample of trials from both control and relevant item sweep sets (separately). We then calculated the average P300 value separately at each virtual site for the selected control and relevant sweeps. Now the actual cross correlation, r, was computed. After 100 iterations of this process, an average of these r values was computed, called ra. We then took the two original single sweep sets and shuffled them together, randomly.

TABLE 5 a list of the 30 sites used in experiment 3 and the virtual sites on which they load significantly (if any)

| site | virtual site |
|---|---|
| FP1 | 3 |
| FP2 | 3 |
| AF3 | 3 |
| AF4 | 3 |
| F7 | |
| F3 | |
| Fz | 2 |
| F4 | 4 |
| F8 | |

TABLE 5-continued a list of the 30 sites used in experiment 3 and the virtual
sites on which they load significantly (if any)

| site | virtual site |
|------|--------------|
| FC5  |              |
| FC1  | 1            |
| FC2  | 2            |
| FC6  |              |
| T7   |              |
| C3   |              |
| Cz   | 1            |
| C4   |              |
| T8   |              |
| CP5  | 1            |
| CP1  | 1            |
| CP2  | 2            |
| CP6  |              |
| P7   |              |
| P3   | 1            |
| Pz   | 1            |
| P4   | 4            |
| P8   |              |
| O1   | 1            |
| Oz   | 4            |
| O2   | 1            |

Virtual site 1 accounts for 31.8% of the variance in the data, virtual site 2 for 17.5%, virtual site 3 15.4%, and virtual site 4 8.9%.

Combining control and relevant sweeps. We now arbitrarily "cut the deck," i.e., we divided the shuffled set, and treated the first fraction of single sweeps as one (pseudo) condition and the second fraction as another. The fraction numbers corresponded to the actual numbers of single sweeps per condition. As previously (with unshuffled data), sweep sets were repeatedly drawn with replacement from each condition, averaged, and the iterated (n=100) cross-correlations (rb) computed. In order to conclude that the subject was guilty of the tested item, the rA value needed to be in the lower 10% tail of the distribution of rb values.

For the unscaled data we used an ANOVA approach. (Although we had noted in the August 2000 progress report that the ANOVA approach wasn't working, we most recently found a correction and the program now does what it is supposed to do.) The plot of P300 amplitudes as a f (virtual site), separately for control (B) and relevant (A) data, lends itself to a 2 (condition) by 4 (virtual site) ANOVA. The approach taken is bootstrapping as with the correlation method, except instead of calculating r, the cross-correlation, we perform an ANOVA on each set of iterated site-condition values (8 in all =4×2). The F-term for interaction states whether the curves from the two conditions are parallel or not. If not, the conclusion is the two profiles differ. The specific criterion here was that the FA-average on real iterated values be in the top 10% tail of the distribution of shuffled FB values.

More detailed summaries of these methods are given below.

Results

The stimulus categories used here were as follows: 1) Relevant items were those accused items (n=either 1 or 2) of which guilty subjects were guilty. 2) Control items were the falsely accused items of which subjects were innocent. 3) Target items were the "Lie Test" items (see above). 4) Irrelevant items were the remaining innocent items not used in false accusation. They have a low probability in our student population (e.g., "ROBBED BANK").

Intra-Individual Diagnoses with Scalp Distributions

This major goal of the originally proposed project was to explore the use of scaled and unscaled scalp distributions as diagnostics of deception. We first insert here a brief summary of the analytic methods used and their acronyms:

Analysis of Scalp Profile (ASP)

This analysis method to be used in these studies is called the analysis of scalp profile (ASP) method. ASP uses a stimulus type by site amplitude interaction analysis as the basis of a decision about guilt or innocence for each subject. One can determine the average amplitude at each virtual site for each stimulus type, and plot pairs of curves. The basic question being answered by ASP is, "Are these curves parallel?" It is expected that for innocent subjects, the control and designated "guilty" or "relevant" stimuli will have parallel curves, whereas for guilty subjects these two stimuli will not yield parallel curves for both scaled and unscaled data. Rather than simply employing an analysis of variance (ANOVA) on the actual raw single sweep data, which are noisy, ASP performs an ANOVA on bootstrapped averages. This ANOVA is not by itself performed to determine significance, but the resulting F value is instead compared with the iterated F values resulting from the second part of ASP. In the first part of the ASP procedure, the actual sample with replacement bootstrapping procedure on real data used in ASP to obtain bootstrapped averages is similar to that used in BAD (see above). From each set of n single sweeps from a particular stimulus, n single sweeps will be randomly drawn with replacement. The same is done at all virtual sites for both stimulus types to be compared. This process is repeated 100 times yielding the number of virtual sites times 100 sets of individual, bootstrapped average P300 values. Now one has a sample size of 100 for each site/item combination and the within individual ANOVA can be carried out on the bootstrapped P300 averages. This is done 50 times and the resulting F-values are averaged. The resulting average F (F-real) is compared with the F-values resulting from part two of ASP.

The only difference between the second part of ASP and the first is that in the second part, prior to random (with replacement) selection of single sweeps to be averaged, the data from both stimulus types are shuffled so that during subsequent random selection, single sweeps are drawn from a set that probably contains both stimulus types. After this procedure, the same ANOVA as performed in part one is performed on the shuffled data to yield an F-value (F-shuffled) for two pseudo groups in which real data were shuffled together thus destroying any real difference between groups (we will call this the base rate). This procedure is now itself performed 100 times to yield a distribution of size 100 of base-rate F-values to which the F-real F-value obtained from part one is compared. If the average F-real value obtained in part one is greater than 90% of the F-shuffled values obtained in part two, then a guilty decision is made, whereas an innocent decision requires that the part one F-value be lower than 40% part two F-values.

ASP will be used on both scaled and unscaled data separately. When performed on scaled data, the results from ASP are orthogonal to those analyzed by BAD because effects of amplitude are removed by the scaling process. The scaling procedure used is the vector length method (McCarthy & Wood, 1985), adapted for individuals. Ordinarily, in group studies, one divides, within a stimulus type (or condition) the average voltage at one site for a subject by the square root of the sum across sites of the squares of mean voltage averages across subjects. Within one subject (for ASP), one divides the voltage for each (virtual) site on each single trial by the square root of the sum of that subject's squared average (across trials) voltages across (virtual) sites.

Correlation Analysis Technique (CAT)

The other intra-individual analysis method for scaled scalp distribution is called the correlation analysis technique (CAT). Its purpose is to test scalp distribution differences as in ASP, but using cross-correlation of the scalp distributions from the two stimuli type conditions, e.g., relevant vs. control. Note that the data are automatically scaled by the correlation process. Part one of this program calculates the actual cross-correlation associated with P300 values of two different stimulus types across sites. This yields a real correlation coefficient (R or R-real) between the two scalp profiles. A guilty subject would likely have a low R when distributions associated with control stimuli are compared with distributions associated with the guilty/relevant stimuli, whereas an innocent subject would have a high R because there is no difference between the designated "guilty/relevant" item and the control stimuli. In order to test the significance of the value of R-real in a given subject, part two of CAT uses a similar procedure to that used in part two of the ASP program. All of the single sweeps from the control and relevant stimuli are shuffled together and then this shuffled set is arbitrarily divided into two pseudosets of sweeps, analogous to cutting a deck of cards. These pseudosets are each separately averaged, and their cross-correlations are then computed. This procedure is done 100 times to create a distribution of 100 R-shuffled values to which to compare the R-real value obtained from the actual data. For a guilty judgment, the real R value should be in the bottom 10% of the distribution of Rs resulting from shuffled data.

Expectations:

1. It is expected that in guilty subjects, the scalp distribution for relevant responses will differ from the scalp distribution for control responses. For innocent subjects, there will be no such differences. This is a wholly novel prediction based on the assumption that truth-telling and deception are two different cognitive states which will differentially engage P300 neurogenerators which will produce differing scalp distributions.

2. It is expected that the simple P300 amplitude at the virtual site containing the major parietal contribution will be larger in response to relevant than in response to control items in guilty subjects, not in innocent subjects. This is based on Rosenfeld et al. (1991) and is examined here simply as a manipulation check.

Results-1

We expect the relevant distribution to differ from the control distribution in guilty persons, but not in innocent persons because for the latter, there are no guilty acts, and therefore, no real relevant items. They can be randomly selected from among the four falsely accused items and designated as relevant.

The nine stimuli used in this study are shown in tabular form (Table 6) below with their symbols, categories (possible Relevant or Control, R/C, or Irrelevant, IR, or Target, TR), and meanings (under ACT):

TABLE 6

| ACT | ACTUAL | STIMULUS | CATEGORY SYMBOL |
|---|---|---|---|
| Stole friend's money | Friend's Money | R/C | F |
| Robbed a bank | Robbed Bank | IR | S |

TABLE 6-continued

| ACT | ACTUAL | STIMULUS | CATEGORY SYMBOL |
|---|---|---|---|
| Used false I.D. | Fake I.D. | R/C | I |
| Broken store window | Store Window | R/C | C |
| Took school records | School Records | IR | T |
| Plagiarized a paper | Plagiarized paper | R/C | A |
| Smoke pot weekly | Pot Weekly | IR | P |
| Stolen a bicycle | Stole Bike | IR | B |
| Taking Lie Test | Lie Test | TR | L |

Recall that we did not know in advance of which guilty act(s) if any the subject would be guilty, and as these differed across subjects, any of the falsely accused items (see methods) could be relevant or guilty in any particular case; hence the designation R/C for the four falsely accused acts. Below (Table 7) is a tabulated distribution of outcomes using symbols from above (any symbols not appearing here indicate acts of which all subjects were innocent):

TABLE 7

| Guilty Item(s) | Number of subjects |
|---|---|
| P and I | 4 |
| F and I | 3 |
| A and I | 1 |
| I | 4 |
| F | 1 |
| B | 1 |
| A | 1 |
| None (innocent) | 7 |

Preliminary analyses revealed that there was no significant difference between amplitudes or distributions (scaled and unscaled) for accused versus non-accused acts of which subjects were innocent. Thus one could simply compare the scalp distribution from a subject for all his guilty/relevant acts (if n>1 or just the single guilty average if n=1) with the average of all remaining, non-target acts. The results of such comparisons (comparison set 1) using only b-p amplitudes as originally proposed for ASP and CAT, along with BAD results (p-p) as a manipulation check (see EXPECTATION 2 above), are tabulated as follows:

TABLE 8a number and percentage of guilty decisions.

| analysis method | guilty subjects | innocent subjects |
|---|---|---|
| BAD (p-p VS1) | 13/16 (81.3%) | 1/7 (14.3%) |
| BAD (p-p, Pz) | 14/16 (87.5%) | 1/7 (14.3%) |
| ASP (scaled) | 4/16 (25%) | 1/7 (14.3%) |
| ASP (unscaled) | 7/16 (43.8%) | 2/7 (28.6%) |
| CAT | 6/16 (37.5%) | 2/7 (28.5%) |

TABLE 8b number and percentage of innocent decisions in experiment.

| analysis method | guilty subjects | innocent subjects |
|---|---|---|
| ASP (scaled) | 2/16 (12.5%) | 1/7 (14.3%) |
| ASP (unscaled) | 0/16 (0%) | 1/7 (14.3%) |
| CAT | 2/16 (12.5%) | 0/7 (0%) |

The following applies to both tables 8a and 8b: Using McNemar's test of differences between correlated proportions, for the guilty subjects, BAD (peak-peak at site Pz)

significantly outperformed unscaled ASP (Z=2.33, p<0.02). There were no significant differences in correct detections between scaled ASP, unscaled ASP, or CAT (p>0.05 for all). Over all analysis methods, there were no significant differences in false positive rates, number of correct innocent decisions, and number of incorrect innocent decisions (p>0.05 for all).

It is noted that for ASP and CAT, analyses were restricted to virtual sites only. It is also seen in Table 8a that BAD (Bootstrapped amplitude difference, relevant vs. control, as in earlier countermeasure experiments, using a 0.95 confidence level) was performed on Virtual Site 1, VS 1, and actual site Pz, and the hit rates were in the 80%-87% range, as we and others usually see in oddball GKT paradigms. This verified that in terms of simple amplitude, the manipulation worked; guilty but not innocent items evoke P300. The result here, however, has further importance in that it shows that this method will work whether subjects are guilty of 1 or 2 items. This was an important and novel finding, not shown before and it will be amplified later with other comparisons of responses to stimuli where the hit rates get into a respectable range using virtual sites, but not with Pz. (We will also argue that preparing a CM for this screening paradigm is not as simple as with a simple GKT.) Using the present comparisons, however, the scalp distribution test results in Table 8a are disappointing. We looked further: T-tests performed on the F-values obtained from part one of ASP for both scaled and unscaled data verify that part one of ASP was in fact yielding higher F values for guilty as opposed to innocent subjects only with unscaled data (t=6.35, p<0.001 for unscaled, t=1.34, P>0.1 for scaled). This suggests that the success in distinguishing guilty and innocent groups with unscaled data is based on amplitude confounded with distribution, not distribution itself. Moreover, group effects, however interesting, do not change the low detection rates in Table 8a. One problem with these comparisons, however, is that one is typically comparing a relatively low number of sweeps (30-60 for one or two guilty items)) with a large number of sweeps (180-210 for 6 or 7 innocent items). Then there is the potential confound of accusation with guilty/innocents, despite our lack of finding of such an effect. The following approach solves these potential confounds.

Results-2

It is noted that prior to undertaking the remaining data analysis, one of the data files from a subject guilty of two acts became corrupted, leaving us 15 guilty subjects (from 16 above), 8 (vs. 9 above) guilty of two acts.

We also did relevant vs. control distribution comparisons (comparison set 2) in which distributions for accused relevant/guilty items (1 or 2) were compared with only accused innocent items (1 or 2), or in which non-accused relevant/guilty items were compared with non-accused innocent items. In the case of the four subjects (see Table 7) guilty of P (not-accused) and I (accused) we compared the combined P and I data with combined B (not accused) and C (accused) data. In the case of innocent subjects, we arbitrarily designated two falsely accused items as "relevant" and used the two other falsely accused items (properly) as controls. Thus, all comparisons in Set 2 are unconfounded by accusation and non-accusation, nor by numbers of trials involved, as they may be in Table 8 above. Table 9, below, has the results, in terms of proportions of guilty calls using the CAT analysis on automatically scaled data; (BAD analysis with Set 2 data is considered below under "Simple Amplitude Effects.")

TABLE 9

Proportions of guilty decisions by CAT algorithm in innocent and guilty groups.

| GUILTY GROUP | | | INNOCENT GROUP | | |
|---|---|---|---|---|---|
| b-p | p-p | b-p or p-p | b-p | p-p | b-p or p-p |
| 6/15 | 8/15 | (11/15) | 0/7 | 0/7 | 0/7 |
| (0.40) | (53.3) | (73.3) | (0) | (0) | (0) |

"b-p" refers to base to peak amplitudes,
"p-p" to peak to peak amplitudes, and
"b-p or p-p" designates the numbers of guilty calls (at 90% confidence levels) using either b-p or p-p analysis.

In the guilty group, the superior p-p method yields only 53% detection with no false positives. However, if one goes to the slightly more liberal "either-or" criterion, the hit rate rises to a slightly higher (and respectable) 73% detection rate, without any increase from 0% false positives in innocents. A Fisher exact test comparing "either-or" proportions in Guilty vs. Innocent subjects yields p<0.05.

Group Data

These are not directly helpful in terms of practical detection of deception, but may help in our understanding of other results. Thus the analyses to be now described are based on comparison set 2 in which relevants and controls are compared in unconfounded tests. The results below in Table 10 are the outputs of 2-way ANOVAs, completely repeated measures, on the factors site (n=4 virtual) and stimulus type (relevant vs. control) in the guilty group.

We will present results on scaled data first, and thus look only at the interaction term, as it is the index of distribution differences unconfounded with amplitude. (With n=7 for the innocent group, it was felt that the concomitant lack of power precluded such test results in that group.)

TABLE 10

These are F and associated P-values for the type by site interactions in the guilty group.

| B-P: | F(3, 42) = 2.143, | P(Greenhouse-Geisser) = .135 |
| P-P | F(3, 42) = 2.11, | P(Greenhouse-Geisser) = .137 |

These values are only at the trend levels, not full significance levels, although for p-p, the Wilks' Lambda, Pillai Trace, and H-L Trace multivariate tests all yielded F=4.58, p<0.03. (These tests for the b-p values yielded p<0.09.) These scaled data (plus the target values) are plotted in the figures below, one for the scaled b-p values, the other for p-p values FIG. 10: Scaled b-p, group-averaged values of 3 stimulus types at 4 virtual sites. These scaled data are shown not to be interpreted, but just to indicate parallel vs. non-parallel curves.

Figure 11:
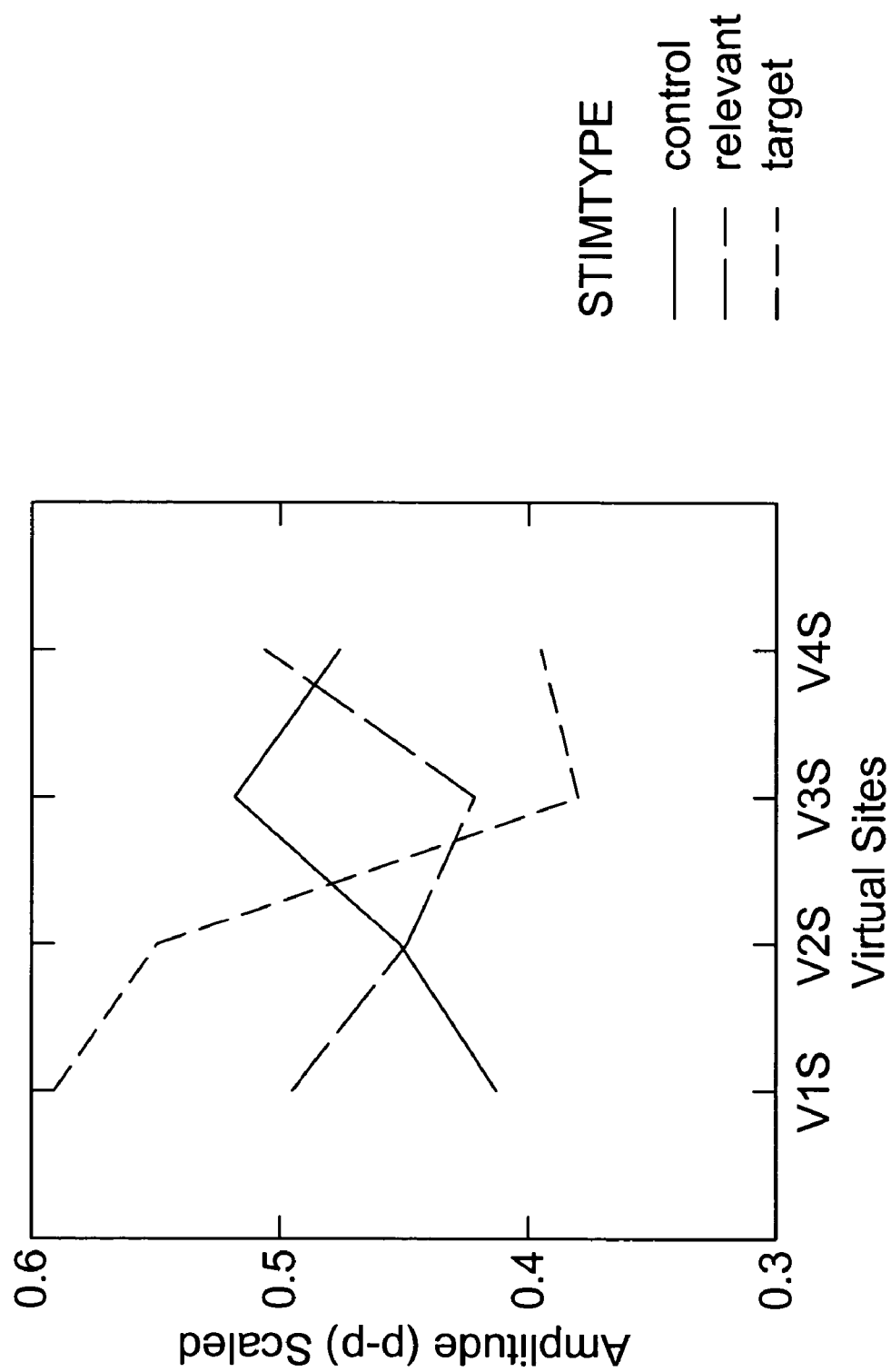
FIG. 11 depicts scaled p-p group-averaged values of 3 stimulus types at 4 virtual sites.

FIG. 11: Scaled p-p group-averaged values of 3 stimulus types at 4 virtual sites. These scaled data are shown not to be interpreted, but just to indicate parallel vs. non-parallel curves.

The relevant and control curves in FIG. 11 look indeed like mirror images and one would have expected an interaction—which one does get in multivariate tests. However, the marginal nature of the results overall suggests, as we already know, that not all subjects are detected with just b-p or just p-p data It also suggests a considerable amount of non-systematic or noise effects in the data. It can be added without showing the individual distribution data that even in those subjects detected with CAT, there was no typical guilty item x site interaction, and there were perhaps only 3-4 (of 15) individuals showing distributions resembling those of the group, as above. There is thus no uniform specific lie distribution seen here.

Figure 10:
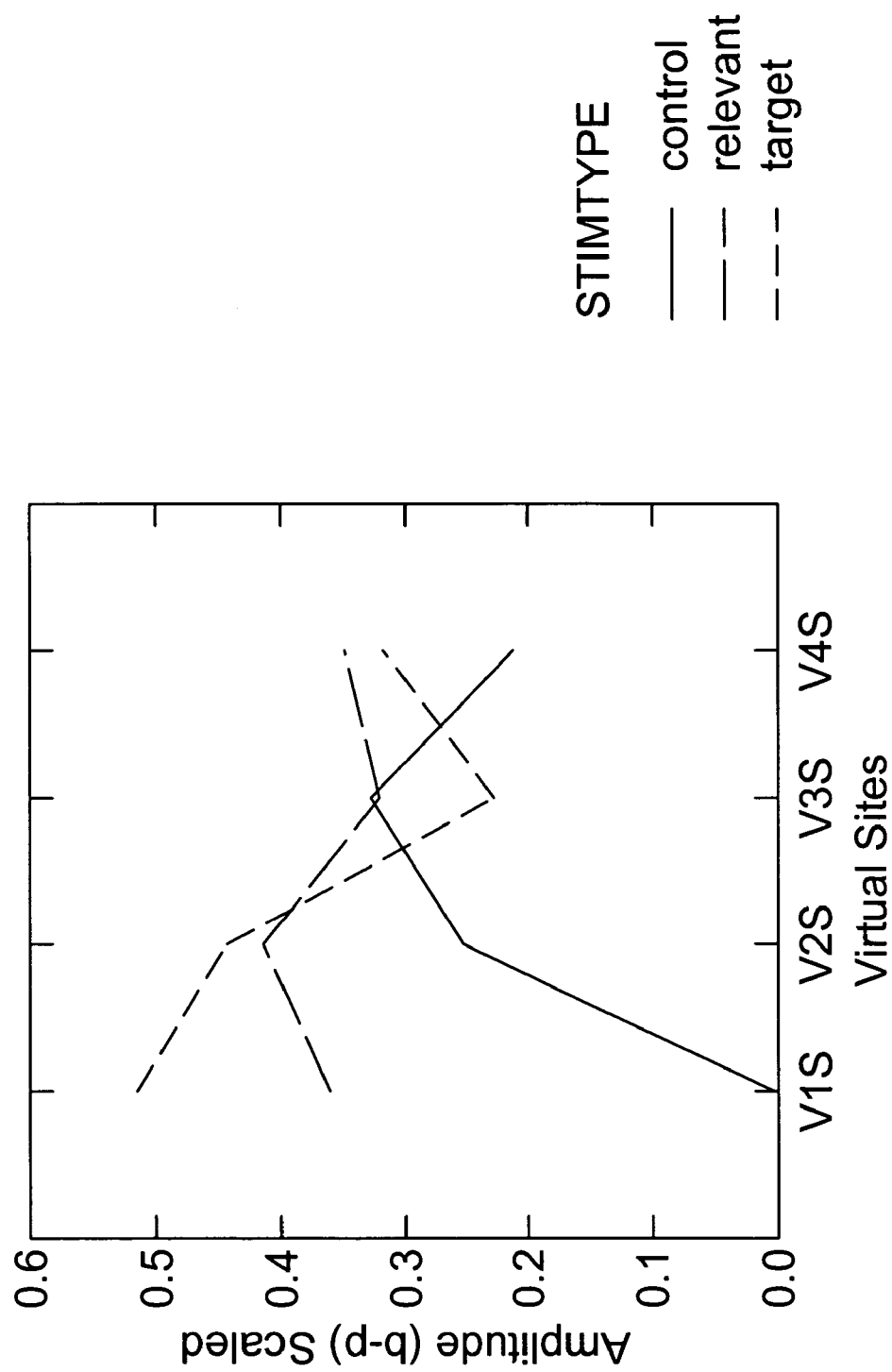
FIG. 10 depicts scaled b-p, group-averaged values of 3 stimulus types at 4 virtual sites.

As a segue into the next section of the results, we now show figures similar to FIGS. 10 and 11 on comparison set 2, except that these are for unscaled data. Thus one can here observe type and site effects, although the interaction effect may confound distribution with amplitude (type) effects.

Figure 12:
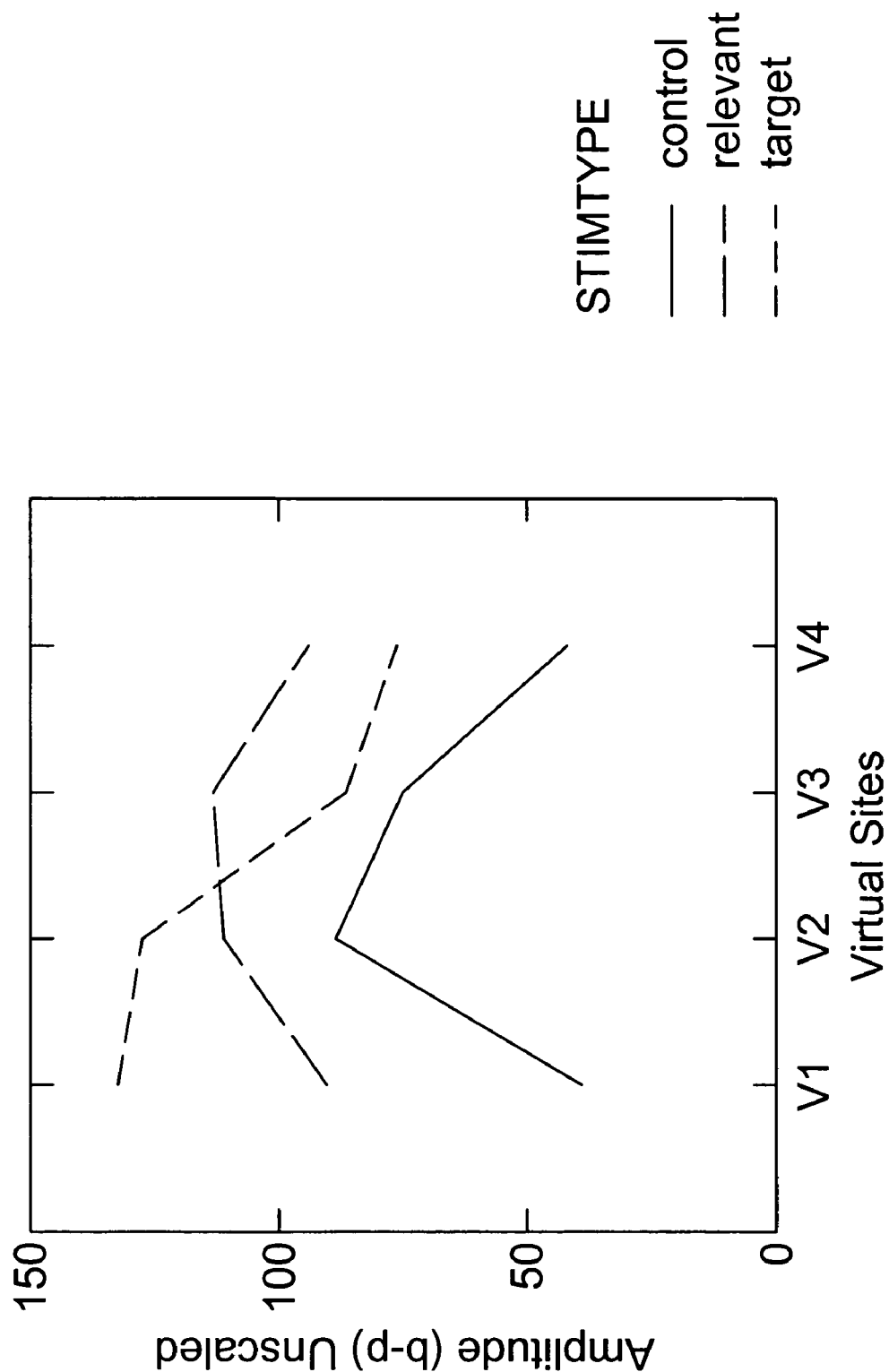
FIG. 12 depicts group's average coded actual b-p amplitudes (10 uV=409.6 units) as a f (virtual site, item type)

FIG. 12: These are the group's average coded actual b-p amplitudes (10 uV=409.6 units) as a f (virtual site, item type).

In FIG. 12, above, the main effect of type (Relevant vs. Control amplitude) was $F(1,14)=3.74$, $p=0.074$. The site effect was not significant, nor was the interaction (both $p>0.3$)

Figure 13:
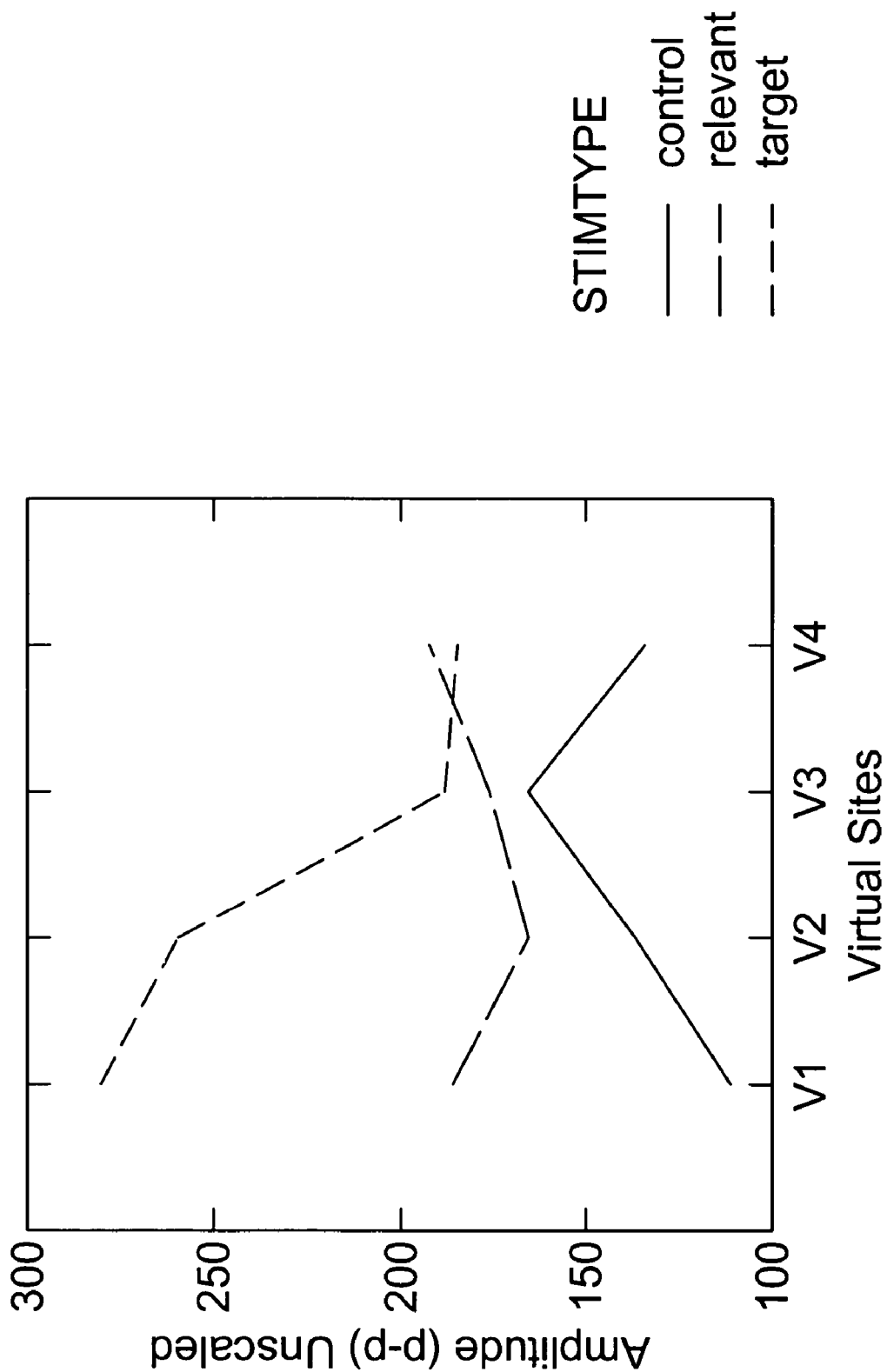
FIG. 13 depicts group's averaged coded actual p-p amplitudes (10 uV=409.6 units) as a f (virtual site, item type).

FIG. 13: These are the group's averaged coded actual p-p amplitudes (10 uV=409.6 units) as a f (virtual site, item type).

Here (FIG. 13), the effect of type was $F(1,14)=5.525$, $p<0.04$. The effect appears maximally carried by the first virtual component, the centro-parietal one. There is no effect of site, which appears to interact with type (although the F[interaction]=2.124, $p=0.123$. This is marginal, but the three multivariate tests on the interaction were all $p<0.05$.)

In the main effect of item, we have the classic oddball amplitude effect in which P300s to rare relevants are bigger than those to frequent controls. This is clearly shown in the grand average ERP figures opening the next section.

Simple Amplitude Effects:

As noted above, the following data do not pertain to the scalp distribution studies except as a simple manipulation check. However, a novel finding emerged, worth reporting.

The following figures show for Virtual Site 1 superimposed grand averages for innocent and guilty groups. For each group, targets and relevants are superimposed, as well as controls and relevants. These averages are based on comparison set 2, where some relevant averages contain one item, and others contain two items, and the comparisons are always symmetrical. First, we have the innocent group. Here there are no real relevant stimuli, so two falsely accused items are designated as "relevant." The other two falsely accused items are combined into a control. It is obvious that control and "relevant " are the same, but target towers over "relevant" (as it would over the similarly small control.)

Figure 14:
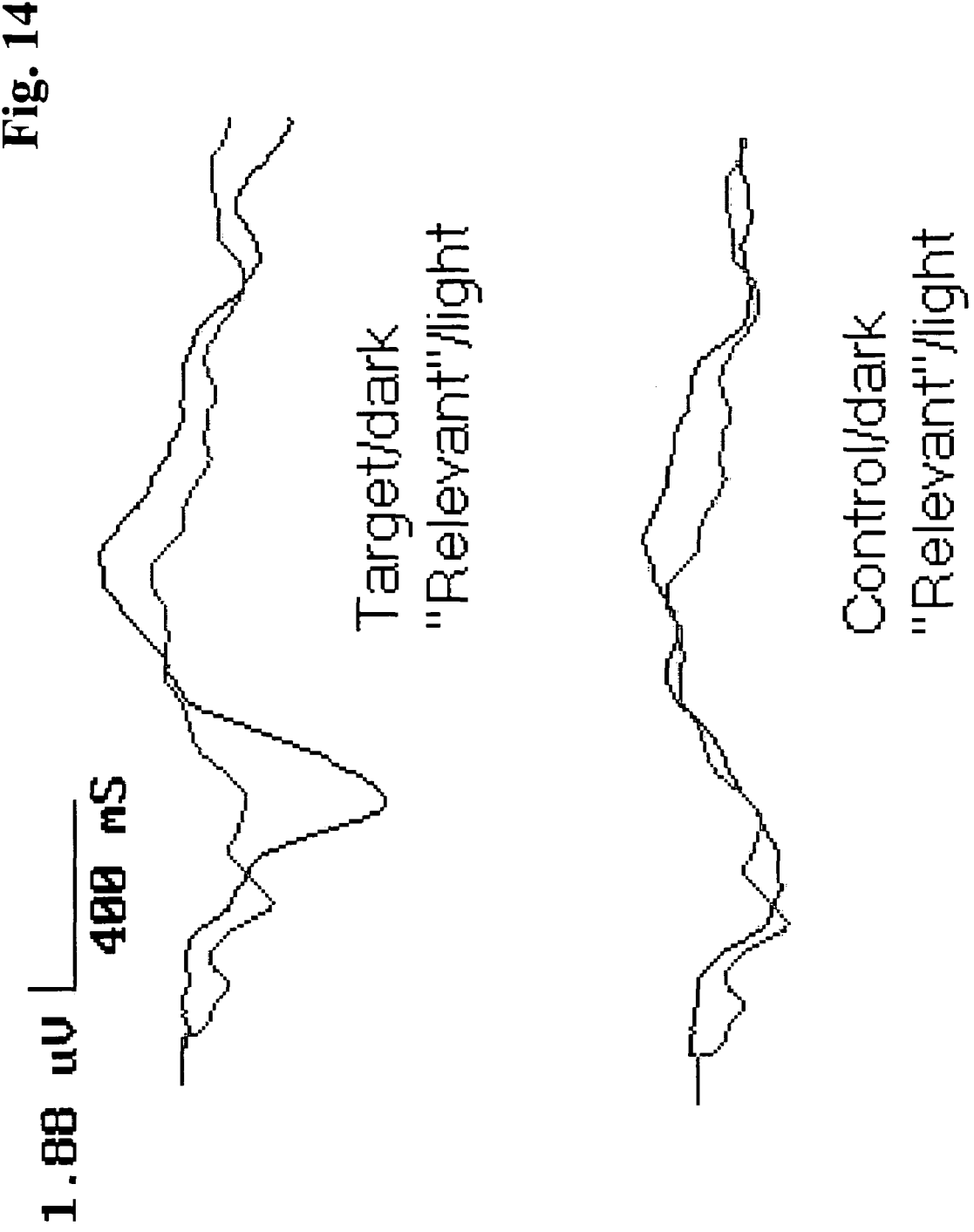
FIG. 14 depicts superimposed grand averages at virtual site 1 in innocent group.

FIG. 14. Superimposed grand averages at virtual site 1 in innocent group.

The following figure shows superimposed grand averages as in FIG. 14, but for the guilty group. It is evident that the target and the relevant, both being real oddballs, both show similar P300s. It is also evident that the relevant item towers over the control.

Figure 15:
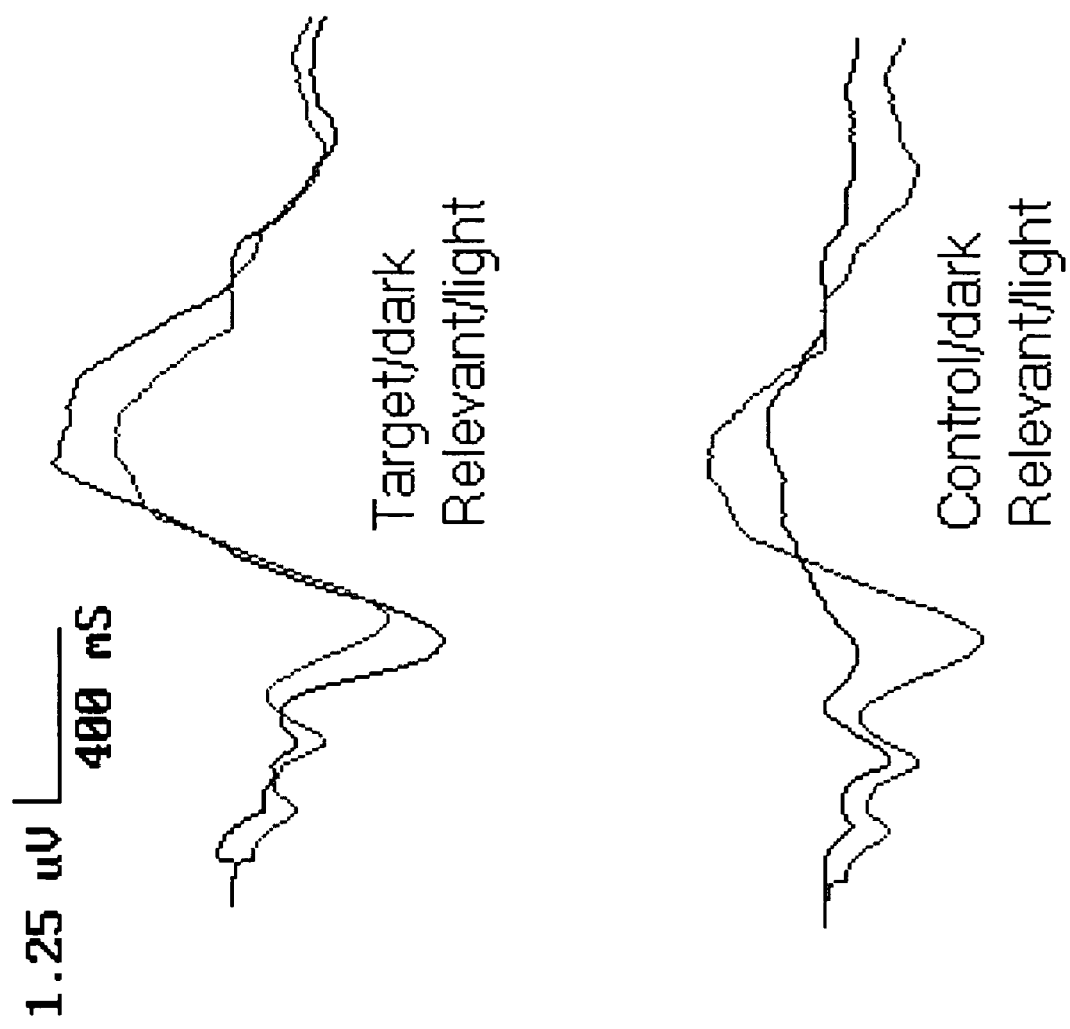
FIG. 15 depicts superimposed grand averages at virtual site 1 (the mostly centro-parietal site) in the guilty group.

FIG. 15: Superimposed grand averages at virtual site 1 (the mostly centro-parietal site) in the guilty group. (Note that what we here designate as relevant items are functionally similar to the probes of the countermeasure studies, and the controls here are analogous to the irrelevants of the CM studies.

Using the BAD method (90% confidence) on V1 only to test within individuals whether relevant is greater than control, 12 of 15 (80%) guilty subjects were correctly classified and there was 0% (%) false positives among the innocents. Multiple relevants made no difference; i.e., 8 of 8 subjects guilty of 2 items were detected as were 4 of 7 subjects guilty of only one item. This is the first time this has been reported using a more natural screening scenario in which subjects could be guilty of more than one item. (In the other uses of this protocol, subjects were controlled to be guilty of only one item; Rosenfeld et al., 1991; Johnson & Rosenfeld, 1992.). We were surprised at this unexpected and unpredicted finding and wondered whether or not simple site Pz would do as well as V1, a virtual site containing much but not exclusively parietal contribution, and certainly more parietal signal than just that from Pz (see FIG. 7, above). Thus we re-did the comparison set 2 data using just the Pz site (as is typically done in P300-based GKT protocols, such as Rosenfeld et. al., 1991, Farwell & Donchin, 1991, Johnson & Rosenfeld, 1992, Allen, et al., 1992). Pz alone afforded poor detection, correctly naming just 6 of 15 (40%) guilty subjects, only 2 of which were guilty of 2 items. This suggests that even for simple amplitude methods, it is worth the trouble to do the PCA so as to determine virtual sites, and is not consistent with Farwell's statements that additional sites don't help (Farwell & Donchin, 1991; Farwell & Smith, 2000). Perhaps using arbitrarily chosen sites (i.e., without the benefit of the PCA) more sites don't help with only one guilty item, but apparently with two (or more?) such items, the additional contributions to the major virtual principal component do help. Of course this novel effect needs looking into and replication.

As a way of beginning this investigation, we generated a third comparison set. From each of the 8 subjects guilty of 2 items, we arbitrarily selected one. For the other 7 guilty subjects guilty of one item, we used that 1 item. For a control, we chose one falsely accused innocent item. Now we repeated BAD (95% confidence) on V1 and on Pz. For V1, 14/15 were detected (93% hit rate). For Pz, only 9/15 (60%) were detected including 5/7 guilty of one item, 4/8 guilty of two items. These results are indeed consistent with the notion that as the number of guilty items within one run increase, the virtual site procedure is increasingly helpful.

Validity of Methods:

In terms of seeing whether or not the intra-individual analyses results confirmed what the eye saw, we finally present some individual graphs showing a visually obvious interaction, and one with obvious lack of interaction.

Figure 16:
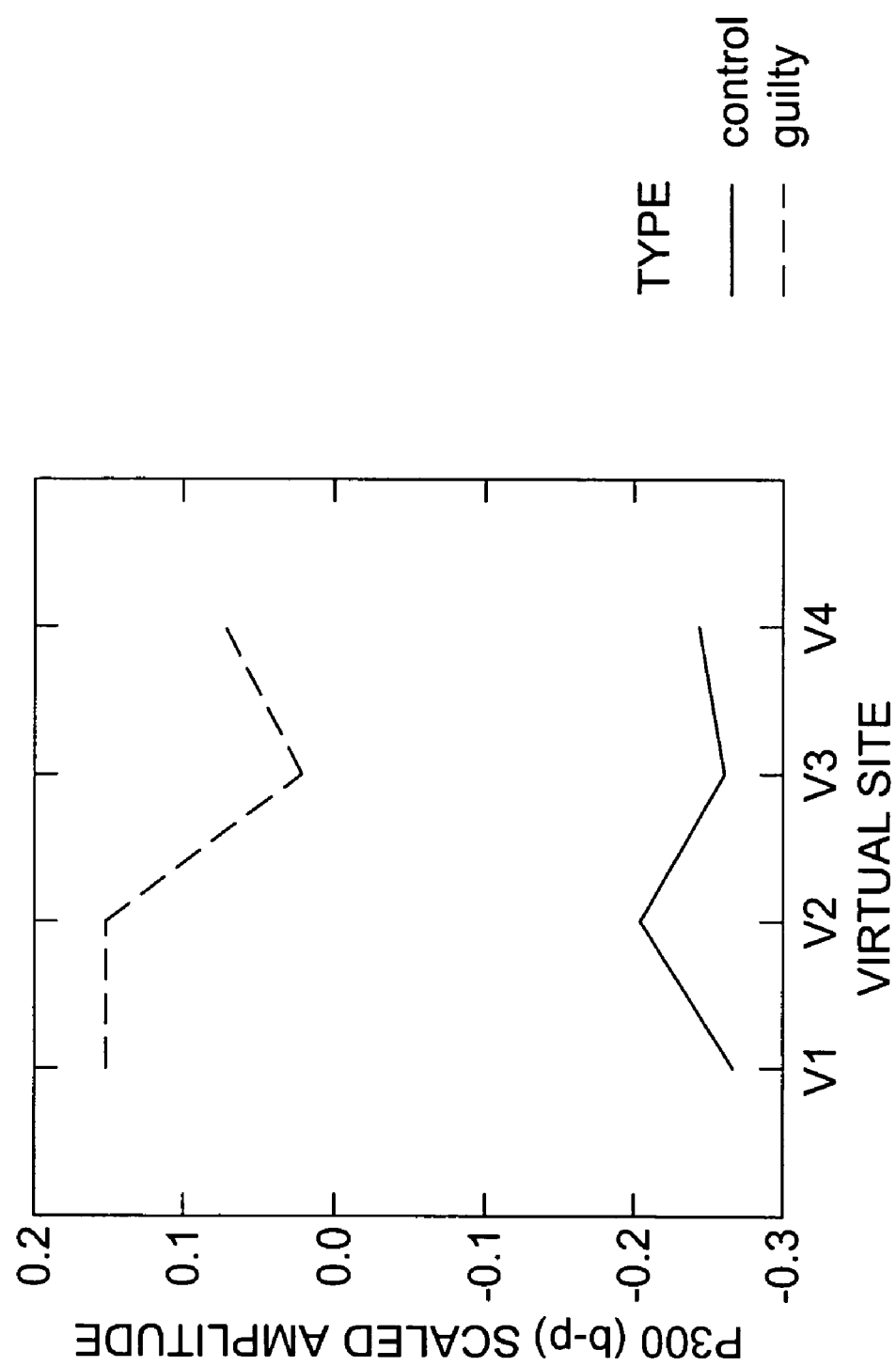
FIG. 16 depicts scaled b-p, group-averaged values of 3 stimulus types at 4 virtual sites from an individual whose relevant (guilty) item distribution did not appear to differ markedly from control item configuration.

FIG. 16: This is from an individual whose relevant (guilty) item distribution did not appear to differ markedly from control item configuration.

It is noted that in all cases where curves were like FIG. 17 (below, containing an obvious interaction), the CAT test found the statistical evidence of interaction. In cases like FIG. 16 (above) where there was clearly no interaction, the CAT program reliably did not detect one. This was true of all subjects in which visually clear outcomes (positive or negative) were obtained, allowing us to comfortably rely on the CAT program for determinations in those other subjects whose outcomes were not visually obvious. (It is noted that these figures are based on the comparison set 2 data in which the comparisons were controlled in terms of accusation; i.e., accused guilty/relevant items were compared only with accused innocent/control items, etc.)

Discussion: Scalp Distribution Study

Regarding the scaled scalp distribution, or profile method of detecting deception, it is not clear from this study how useful the method may become. We saw that by using either a positive outcome from CAT on b-p or p-p profiles, we could detect 73% of the guilty subjects, with 0% false positives in innocent subjects tested with the same criterion. These results were based on the least confounded comparisons within subjects regarding accused versus non-accused items. That is respectable, but needs replication and improvement. More importantly, this method requires more systematic investigation with respect to guilt criteria used in the CAT algorithm as well as effects of accusation. Time did not permit us to systematically vary confidence level in this study. That is, for a guilty decision, the CAT method we use requires (as rationalized above) that the real cross correlation coefficient between relevant and control items across sites be in the bottom 10% of the distribution of shuffled, bootstrapped cross-correlations; i.e., we operate at the 90% confidence level. Perhaps this is too stringent. Perhaps the CAT method is so sensitive that if we dropped the confidence level to 80% or less, we would begin approaching 90 to 100% detection of guilty subjects with little or no cost in false positive rate. We did not see the point in pursuing this with the present data set because we had only seven innocent subjects, and because the guilty subject set contained a highly variable set of guilty acts per subject (see Table 7 above), some of which were accused, some not. This was the result of our electing to use a very naturalistic screening scenario of the type the government might find useful.

In future work, in view of the promise seen here with appropriate, unconfounded comparisons (set 2), it will be worthwhile to better control the accusation factor. In this regard, it must be mentioned that the demographics at this university must have changed since we last used this protocol 20 or more years ago. At that time, the item "used false ID" was one of which 50% of the student subjects could be counted upon to have committed. In contrast, none of the students in the 1980s reported stealing friends' monies. Sadly, this has changed. Some careful demographic piloting next time might allow us choose a list of items resulting in more predictable guilt profiles.

We conclude that the profile method is worth pursuing, because it does not seem as if there can be a simple countermeasure made readily available. It was self evident to our laboratory from the earliest days of P300 based detection of deception with P300 as a recognition index in GKT paradigms, that it would be possible to covertly make irrelevants relevant and thereby defeat the test. We strongly suspected that this could be done because the determinants of P300 amplitude were well-known—low subjective probability, task relevants and/or meaningfulness—and we knew that the methods described above for covertly increasing the meaningfulness and task relevants of irrelevant stimuli were readily implemented. This was clearly demonstrated empirically in the earlier portion of this report. In contrast, the specific psychological/behavioral factors of scalp distribution shapes are not well-known and have barely been studied. Even in our published demonstrations of differing profiles during deception vs. truthtelling in simpler paradigms than the present one, we did not know why deception produced one profile, truth-telling produced another. We could but speculate that deceptive and truthful mind states differentially engaged neuronal systems in different ways. This is a highly abstract formulation, however, and one still has no idea how to alter a brain map of any kind in any way.

We have ourselves chosen in several previous papers and even here in the countermeasure studies to compare averaged probe P300 amplitudes to the average of responses to all irrelevants, despite the fact that this comparison inevitably entails comparing an average with relatively low numbers of single sweeps to an average based on relatively high numbers of single sweeps. These comparisons involved not profile, but simple amplitude at one site. In these studies, typically large control groups of innocent subjects or conditions has allowed us to show that there are virtually no false positives with these numerically asymmetrical comparisons in simple autobiographical oddball recognition paradigms. For the following reasons, the same arguments probably do not apply when the comparisons made are between profiles:

1) Empirically, Table 8a above showed that using comparisons of guilty/relevant items with all innocent (irrelevant) items afforded only 6/16 (37.5%) correct detections (from CAT) but with 2/7 (28.5%) false positives. These were based on b-p values, but if one used an either/or (bp-pp) criterion (as in Table 9) there would have been only 1 more correct detection, accompanied by 1 more false positive; the percentages just given would become 44% and 43%. Of course with the hit and false positive rates at virtually the same low level, this method is worthless. In comparison, Table 9 showed that with unconfounded comparisons within subjects, the either/or criterion yielded 73% detection against 0% false positives.

2) More theoretically, by averaging all irrelevant/innocent response profiles together, one is more likely to get a null profile to be compared with a profile for just one or two guilty (relevant) guilty act(s). It is conceivable that each stimulus type, whether guilty or innocent, whether accused or not, could generate a profile influenced in part by the specific nature of the specific act represented. Averaging across all irrelevant acts will tend to cancel these effects in averages of many items. This would not happen with simple P300 amplitude. The P300 amplitude depends on factors quite apart from the specific meanings of evoking stimuli, namely, subjective probability and relevants. Thus, there are typically no or very small P300s to each innocent irrelevant, apart from specific meanings. Averaging them removes only noise. This means, as we saw, that the comparison set 1 approach will work with simple amplitude at one site, but not with profile.

3) Finally, to the extent that the older simple P300 amplitude index of recognition may be used, it will definitely profit by use on a virtual site extracted with a spatial PCA.

REFERENCES

Allen, J., Iacono, W. G. and Danielson, K. D. (1992). The identification of concealed memories using the event-related potential and implicit behavioral measures: A methodology for prediction in the face of individual differences. *Psychophysiology,* 29, 504-522.

Catell, R. B. (1966). The scree test for the number of factors. *Multivariate Behavioral Research,* 1, 245-276.

Donchin, E., Spencer, K., & Dien (1997). The varieties of deviant experience: ERP manifestation of deviance processors in Van Boxtel, G. J. M. & Bocken, K. B. E. (Eds.), *Brain and Behavior: Past, Present, and Future,* Tilburg University Press, p. 116.

Ellwanger, J., Rosenfeld, J. P., Sweet, J. J. & Bhatt, M. (1996). Detecting simulated amnesia for autobiographical and recently learned information using the P300 event-related potential. *International Journal of Psychophysiology,* 23, 9-23.

Ellwanger, J., Rosenfeld, J. P., Hannkin, L. B., & Sweet, J. J. (1999). P300 as an index of recognition in a standard and difficult match-to-sample test: A model of Amnesia in normal adults. *The Clinical Neuropsychologist,* 13, 100-108.

Fabiani, M., Gratton, G., Karis, D., & Donchin, E (1987). The definition, identification, and reliability of measurement of the P3 component of the event-related potential. In P. K. Ackles, J. R. Jennings, & M. G. H. Coles (Eds.), *Advances in psychophysiology* Vol. 2, Greenwich: JAI Press.

Farwell, L. A., & Donchin, E. (1991). The truth will out: Interrogative polygraphy ("lie detection") with event-related potentials. *Psychophysiology*, 28, 531-547.

Farwell, L. A. & Smith, S. S. (2001). Using Brain MERMER Testing to Detect Knowledge Despite Efforts to Conceal. *J. Forensic Sciences.* 46 (1), 1-9.

Johnson, M. M., & Rosenfeld, J. P. 1992). Oddball-evoked P300-based method of deception detection in the laboratory II: Utilization of non-selective activation of relevant knowledge. *International Journal of Psychophysiology*, 12, 289-306.

Johnson, R., Jr. (1988). The amplitude of the P300 component of the event-related potential. In P. K. Ackles, J. R. Jennings, & M. G. H. Coles (Eds.), *Advances in psychophysiology*, Vol. 2 (pp. 69-138). Greenwich, Conn.: JAI Press.

Johnson, R. (1993). On the neural generators of the P300 component of the event-related potential. *Psychophysiology*, 30, 90-97.

Lykken, D. T. (1981). *A tremor in the blood*. New York: McGraw-Hill.

McCarthy, G. & Wood, C. (1985). Scalp distributions of event-related potentials: an ambiguity associated with analysis of variance models. *Electroenceph. Clin. Neurophysiol.*, 62, 203-208.

Miller, A. R. (1999a). P300 amplitude and topography in pseudomemory phenomena. Unpublished Doctoral Dissertation, Northwestern University, Evanston, Ill., pp 11-59.

Miller, A. R. (1999b). P300 amplitude and topography in pseudomemory phenomena. Unpublished Doctoral Dissertation, Northwestern University, Evanston, Ill., pp 60-122.

Miller, A. R., Rosenfeld, J. P., et al. (2002). P300 amplitude and topography distinguish between honest performance and feigned amnesia in an autobiographical oddball task. *J. Psychophysiology*, 16, 1-11.

Pivik, R. T., Broughton, R., Coppola, R., Davidson, R. J., Fox, N., & Nuwer, M. (1993). Guidelines for the recording and quantitative analysis of electroencephalographic activity in research contexts. *Psychophysiology*, 30, 547-558.

Rosenfeld, J. P., Angell, A., Johnson, M., & Qian, J. (1991). An ERP-based, control-question lie detector analog: Algorithms for discriminating effects within individuals' average waveforms. *Psychophysiology*, 38, 319-335.

Rosenfeld, J. P., Cantwell, G., Nasman, V. T., Wojdac, V., Ivanov, S., & Mazzeri, L. (1988). A modified, event-related potential-based guilty knowledge test. *International Journal of Neuroscience*, 24, 157-161.

Rosenfeld, J. P., Ellwanger, J. W., Nolan, K., Wu, S., Bermann, & Sweet, J. J. (1999). P300 scalp amplitude distribution as an index of deception in a simulated cognitive deficit model. *Int. J. Psychophysiol.*, 33(1), 3-20.

Rosenfeld, J. P., Reinhart, A. M., Bhatt, M., Ellwanger, J., Gora, K., Sekera, M., & Sweet, J. (1998). P300 Correlates of simulated amnesia on a matching-to-sample task: Topographic analyses of deception vs. truth-telling responses. *International Journal of Psychophysiology*, 28, 233-248.

Rosenfeld, J. Peter, Rao, Archana, Soskins, M., and Miller, A. R. (2002) P300 Scalp Distribution as an Index of Deception: Control for Task Demand. *Journal of Credibility Assessment and Witness Psychology.* 3 (1) 1-22. [Internet Journal]

Rosenfeld, J. P., Rao, A., Soskins, & Miller (submitted). Scaled P300 scalp distribution correlates of deception in an autobiographical oddball paradigm.

Seymour, T. L., Seifert, C. M., Shafto, M. G., Mosmann, A. L., (2000). Using response time measures to assess "guilty knowledge". *Journal of Applied Psychology*, 85 (1), 30-37

Soskins, M., Rosenfeld, J. P., & Niendam, T. (2001). The case for peak-to-peak measurement of P300 recorded at 0.3 hz high pass filter settings in detection of deception. *Int. J. Psychophysiology*, 40, 173-180. Srebro, R. (1996). A Bootstrap method to compare the shapes of two scalp fields. *Electroenceph. Clin. Neurophysiol.*, 100, 25-32.

United States General Accounting Office (2001) *Report to Hon. Charles E. Grassley, U.S. Senate Investigative Techniques: Federal Agency Views on the Potential of "Brain Fingerprinting."* USGAO: GAO-02-22

Wasserman, S., & Bockenholt, U. (1989). Bootstrapping: Applications to psychophysiology. *Psychophysiology*, 26, 208-221.

I Claim:

1. A method of inferring deception comprising:

(a) presenting a first item of a plurality of items to a subject, the first item comprising subject matter likely unfamiliar to the subject, the presentation having a first attribute of a plurality of attributes, each of the plurality of items comprising a subject matter which is comprehensible to the subject independent of the plurality of attributes;

(b) waiting for a first duration substantially unpredictable by the subject;

(c) changing, upon expiration of the first duration, the presentation of the first item from the first attribute to one of a second or third attribute, the second attribute being different from the first attribute, the third attribute being different from the second attribute, wherein the presentation of the first item is more likely to be changed from the first attribute to the third attribute than from the first attribute to the second attribute;

(d) recording a first parameter indicative of brain activity of the subject during at least one of the presenting of the first item, waiting, changing, or combinations thereof;

(e) presenting a second item of the plurality of items to the subject, the second item comprising subject matter of questionable familiarity to the subject, the presentation having the first attribute;

(f) waiting for a second duration substantially unpredictable by the subject;

(g) changing, upon expiration of the second duration, the presentation of the second item from the first attribute to one of the second or third attributes, wherein the presentation of the second item is more likely to be changed from the first attribute to the third attribute than from the first attribute to the second attribute;

(h) recording a second parameter indicative of brain activity of the subject during at least one of the presenting of the second item, waiting, changing, or combinations thereof; and (i) determining, based on the first and second parameters, whether the subject has prior familiarity with the subject matter of the second item.

2. The method of claim 1 further comprising:
(j) instructing the subject to provide a first acknowledgment of the presentation of each of the plurality of items having the first attribute, provide a second acknowledgement of the presentation of each of the plurality of items having the second attribute, and provide a third acknowledgement of the presentation of each of the plurality of items having the third attribute.

3. The method of claim 2, further comprising:
(k) receiving the first acknowledgment in response to the presenting of the first item with the first attribute; and
(l) receiving the first acknowledgment in response to the presenting of the second item having the first attribute.

4. The method of claim 3 further comprising:
(m) measuring a delay between at least one of (a) and (k), (e) and (l), or combinations thereof.

5. The method of claim 4 further comprising:
(n) determining whether the subject is using a countermeasure based on the measured delay.

6. The method of claim 2, further comprising:
(k) receiving one of the second or third acknowledgments from the subject in response to the changing of the presentation of the first item; and
(l) receiving one of the second or third acknowledgments from the subject in response to the changing of the presentation of the second item.

7. The method of claim 6 further comprising:
(m) measuring a delay between at least one of (c) and (k), (g) and (l), or combinations thereof.

8. The method of claim 7, further comprising:
(n) determining whether the subject is paying attention based on the measured delay.

9. The method of claim 2 wherein the first acknowledgement comprises pressing a first button to generate a first signal, the second acknowledgment comprises pressing a second button to generate a second signal and the third acknowledgement comprises pressing a third button to generate a third signal.

10. The method of claim 1 wherein the each of the plurality of items comprises an alphanumeric item.

11. The method of claim 1 wherein the first, second and third attributes each comprise a different color.

12. The method of claim 1 wherein each of the first and second durations range from approximately 1400 to approximately 1850 ms.

13. The method of claim 1 wherein the first and second parameters each comprise comprise a p300 brain wave.

14. The method of claim 1, further comprising receiving a claim by the subject as to their familiarity with the subject matter, the determining further comprising determining the likely truthfulness of the subject in relation to the claim.

15. The method of claim 1 further comprising:
(j) repeating (a) through (i), wherein the subject matter of the first and second items is changed with each repetition.

16. The method of claim 15, wherein the repeating is performed for at least 20 repetitions.

17. The method of claim 15, wherein at least a portion of the subject matter comprises autobiographical subject matter related to the subject.

18. The method of claim 1, wherein (e)-(h) are performed prior to (a)-(d).

19. The method of claim 1, wherein (i) further comprises comparing the first parameter with the second parameter.

20. The method of claim 1, wherein one of the second and third attributes may obscure the subject matter of the first and second items as presented.

21. The method of claim 1, wherein each of the first and second items comprise at least one alphanumeric string comprising a first at least one alphanumeric character, the second attribute comprising a substitution of a second at least one alphanumeric character for the first alphanumeric character and the third attribute comprising a substitution of a third at least one alphanumeric character for the first alphanumeric character, the second at least one alphanumeric character being different from the third at least one alphanumeric character.

22. A system for inferring deception comprising:
first logic coupled with a display and operative to present a first item of a plurality of items to a subject, the first item comprising subject matter likely unfamiliar to the subject, the presentation having a first attribute of a plurality of attributes, each of the plurality of items comprising a subject matter which is comprehensible to the subject independent of the plurality of attributes;
a timer operative to wait for a first duration substantially unpredictable by the subject;
second logic coupled with the timer and the display and, upon expiration of the first duration, operative to change the presentation of the first item on the display from the first attribute to one of a second or third attribute, the second attribute being different from the first attribute, the third attribute being different from the second attribute, wherein the presentation of the first item is more likely to be changed from the first attribute to the third attribute than from the first attribute to the second attribute;
a recorder adapted to be coupled with the subject and operative to record a first parameter indicative of brain activity of the subject during at least one of the presentation of the first item, waiting, changing, or combinations thereof;
third logic coupled with the display and operative to present a second item of the plurality of items to the subject, the second item comprising subject matter of questionable familiarity to the subject, the presentation having the first attribute;
wherein the timer is further operative to wait for a second duration substantially unpredictable by the subject;
fourth logic coupled with the timer and the display and, upon expiration of the second duration, operative to change the presentation of the second item from the first attribute to one of the second or third attributes, wherein the presentation of the second item is more likely to be changed from the first attribute to the third attribute than from the first attribute to the second attribute;
wherein the recorder is further operative to record a second parameter indicative of brain activity of the subject during at least one of the presentation of the second item, waiting, changing, or combinations thereof and
fifth logic coupled with the recorder and operative to determine, based on the first and second parameters, whether the subject has prior familiarity with the subject matter of the second item.

23. The system of claim 22 further comprising:
an instruction operative to instruct the subject to provide a first acknowledgment of the presentation of each of the plurality of items having the first attribute, provide a second acknowledgement of the presentation of each of the plurality of items having the second attribute, and provide a third acknowledgement of the presentation of each of the plurality of items having the third attribute.

24. The system of claim 23, further comprising:
a first interface coupled with the first logic and operative to receive the first acknowledgment in response to the presenting of the first item with the first attribute; and
a second interface coupled with the third logic and operative to receive the first acknowledgment in response to the presenting of the second item having the first attribute.

25. The system of claim 24 further comprising:
sixth logic coupled with the first and second interfaces and the first and third logic and operative to measure a delay between at least one of the presentation of the first item with the first attribute and the receiving of the first acknowledgement, the presentation of the second item with the first attribute and the receiving of the first acknowledgement, or combinations thereof.

26. The system of claim 25 wherein the sixth logic is further operative to determine whether the subject is using a countermeasure based on the measured delay.

27. The system of claim 23, further comprising:
a first interface coupled with the second logic and operative to receive one of the second or third acknowledgments from the subject in response to the changing of the presentation of the first item; and
a second interface coupled with the fourth logic and operative to receive one of the second or third acknowledgments from the subject in response to the changing of the presentation of the second item.

28. The system of claim 27 further comprising:
sixth logic coupled with the first and second interfaces and the second and fourth logic and operative to measure a delay between at least one of the presentation of the first item with the second or third attributes and the receiving of the second or third acknowledgements, the presentation of the second item with the second or third attributes and the receiving of the second or third acknowledgements, or combinations thereof.

29. The system of claim 28 wherein the sixth logic is further operative to determine whether the subject is paying attention based on the measured delay.

30. The system of claim 23 wherein the first acknowledgement comprises pressing a first button on a first interface to generate a first signal, the second acknowledgment comprises pressing a second button on a second interface to generate a second signal and the third acknowledgement comprises pressing a third button on a third interface to generate a third signal.

31. The system of claim 22 wherein each of the first and second durations range from approximately 1400 to approximately 1850 ms.

32. The system of claim 22 wherein the first and second parameters comprise at least one p300 brain wave.

33. The system of claim 22, further comprising receiving a claim by the subject as to their familiarity with the subject matter, the fifth logic being further operative to determine the likely truthfulness of the subject in relation to the claim.

34. The system of claim 22 wherein the first logic, timer, second logic, recorder, third logic and fourth logic are repeatedly utilized wherein the subject matter of the first and second items is changed with each repetition.

35. The system of claim 34, wherein the repeating is performed for at least 20 repetitions.

36. The system of claim 34, wherein at least a portion of the subject matter comprises autobiographical subject matter related to the subject.

37. The system of claim 22, wherein presentation of the second item occurs prior to the presentation of the first item.

38. The system of claim 22, wherein the fifth logic is further operative to compare the first parameter with the second parameter.

39. The system of claim 22 wherein the each of the plurality of items comprises an alphanumeric item.

40. The system of claim 22 wherein the first, second and third attributes each comprise a different color.

41. An apparatus for inferring deception comprising:
means for presenting a first item of a plurality of items to a subject, the first item comprising subject matter likely unfamiliar to the subject, the presentation having a first attribute of a plurality of attributes, each of the plurality of items comprising a subject matter which is comprehensible to the subject independent of the plurality of attributes;
means for waiting for a first duration substantially unpredictable by the subject;
means for changing, upon expiration of the first duration, the presentation of the first item from the first attribute to one of a second or third attribute, the second attribute being different from the first attribute, the third attribute being different from the second attribute, wherein the presentation of the first item is more likely to be changed from the first attribute to the third attribute than from the first attribute to the second attribute;
means for recording a first parameter indicative of brain activity of the subject during at least one of the presenting of the first item, waiting, changing, or combinations thereof;
means for presenting a second item of the plurality of items to the subject, the second item comprising subject matter of questionable familiarity to the subject, the presentation having the first attribute;
means for waiting for a second duration substantially unpredictable by the subject;
means for changing, upon expiration of the second duration, the presentation of the second item from the first attribute to one of the second or third attributes, wherein the presentation of the second item is more likely to be changed from the first attribute to the third attribute than from the first attribute to the second attribute;
means for recording a second parameter indicative of brain activity of the subject during at least one of the presenting of the second item, waiting, changing, or combinations thereof; and
means for determining, based on the first and second parameters, whether the subject has prior familiarity with the subject matter of the second item.

42. A method of inferring deception comprising:
(a) providing a first item comprising subject matter which is likely unfamiliar to a subject independent of the subject's comprehension of the subject matter;
(b) providing a second item comprising subject matter which is of questionable prior familiarity to the subject independent of the subject's comprehension of the subject matter;
(c) providing a third item;
(d) instructing the subject to provide a first acknowledgment in response to a presentation of the third item;
(e) providing a fourth item different from the first, second and third items;
(f) instructing the subject to provide a second acknowledgment in response to a presentation of the fourth item, the second acknowledgement being different from the first acknowledgement;

(g) presenting the first item to the subject;

(h) waiting for a first duration substantially unpredictable by the subject;

(i) selecting and presenting, upon expiration of the first duration, one of the third or fourth items, the selection of which being substantially unpredictable by the subject;

(j) recording a first parameter indicative of brain activity of the subject during at least one of (g), (h), (i), or combinations thereof;

(k) presenting the second item to the subject;

(l) waiting for a second duration substantially unpredictable by the subject;

(m) selecting and presenting, upon expiration of the second duration, one of the third or fourth items, the selection of which being substantially unpredictable by the subject;

(n) recording a second parameter indicative of brain activity of the subject during at least one of (k), (l), (m), or combinations thereof and (o) determining, based on the first and second parameters, whether the subject has prior familiarity with the subject matter of the second item.

43. The method of claim 42, further comprising:

(p) instructing the subject to provide a third acknowledgment in response to a presentation of the first item, the third acknowledgement being different from the second acknowledgement; and (q) instructing the subject to provide a fourth acknowledgment in response to a presentation of the second item, the fourth acknowledgement being different from the second acknowledgement.

* * * * *

UNITED STATES PATENT AND TRADEMARK OFFICE
CERTIFICATE OF CORRECTION

PATENT NO. : 7,376,459 B2
APPLICATION NO. : 11/224523
DATED : May 20, 2008
INVENTOR(S) : J. Peter Rosenfeld et al.

It is certified that error appears in the above-identified patent and that said Letters Patent is hereby corrected as shown below:

On the Title Page

Page 2, in column 2, line 30, after "Address, 1980" delete "Suprisel" and substitute --Surprise-- in its place.

Page 3, in column 1, line 5, before "Fail the Truth" delete "Detector" and substitute --Detectors-- in its place.

Page 3, in column 1, line 17, after "Jul. 1984," delete "vol. 29" and substitute --vol. 39-- in its place.

Page 3, in column 1, line 20, before "American Psychologist" delete "publicatin," and substitute --publication,-- in its place.

Page 3, in column 2, line 5, after "Assessment and" delete "Milingering:" and substitute --Malingering:-- in its place.

Page 3, in column 2, line 7, before "of Clinical" delete "Archies" and substitute --Archives-- in its place.

Page 3, in column 2, line 12, before "and Leininger," delete "Giullano" and substitute --Giuliano-- in its place.

Page 3, in column 2, line 26, after "*Mental Health*", delete "*Practive*" and substitute --*Practice*-- in its place.

UNITED STATES PATENT AND TRADEMARK OFFICE
CERTIFICATE OF CORRECTION

PATENT NO.         : 7,376,459 B2
APPLICATION NO. : 11/224523
DATED              : May 20, 2008
INVENTOR(S)       : J. Peter Rosenfeld et al.

It is certified that error appears in the above-identified patent and that said Letters Patent is hereby corrected as shown below:

In the Claims

In column 42, claim 22, line 55, immediately after "thereof" insert --;--.

Signed and Sealed this

Seventh Day of April, 2009

JOHN DOLL
*Acting Director of the United States Patent and Trademark Office*